(12) United States Patent
Walls

(10) Patent No.: US 8,115,640 B2
(45) Date of Patent: Feb. 14, 2012

(54) IMPLANTABLE MEDICAL DEVICE ALERT MANAGEMENT

(75) Inventor: George L. Walls, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 316 days.

(21) Appl. No.: 12/273,498

(22) Filed: Nov. 18, 2008

(65) Prior Publication Data

US 2010/0123587 A1 May 20, 2010

(51) Int. Cl.
*G08B 23/00* (2006.01)

(52) U.S. Cl. ............... 340/573.1; 340/573.4; 340/572.1; 340/572.4; 340/572.8; 600/300; 600/301; 600/323; 600/365; 600/509; 600/516; 607/32; 607/60

(58) Field of Classification Search ............... 340/573.1, 340/573.4, 572.1, 572.4, 572.8; 600/300, 600/301, 323, 365, 509, 516; 607/32, 60
See application file for complete search history.

(56) References Cited

U.S. PATENT DOCUMENTS

| | | | |
|---|---|---|---|
| 6,766,198 B1 * | 7/2004 | Snell | 607/30 |
| 7,120,488 B2 | 10/2006 | Nova et al. | |
| 2002/0052539 A1 | 5/2002 | Haller et al. | |
| 2002/0082665 A1 * | 6/2002 | Haller et al. | 607/60 |
| 2002/0198473 A1 | 12/2002 | Kumar et al. | |
| 2003/0172940 A1 * | 9/2003 | Rogers et al. | 128/899 |
| 2005/0021370 A1 | 1/2005 | Riff et al. | |
| 2006/0052842 A1 | 3/2006 | Hess et al. | |
| 2007/0179389 A1 * | 8/2007 | Wariar | 600/508 |
| 2008/0183091 A1 * | 7/2008 | Fischell et al. | 600/509 |

FOREIGN PATENT DOCUMENTS

WO 0201777 3/2002

* cited by examiner

*Primary Examiner* — Tai T Nguyen

(57) ABSTRACT

Exemplary systems and methods for automatically managing implantable medical device (IMD) related alerts are described. One method receives implantable medical device-related alerts. The method automatically manages the implantable medical device alerts by parsing the alerts through a set of predefined parameters.

14 Claims, 15 Drawing Sheets

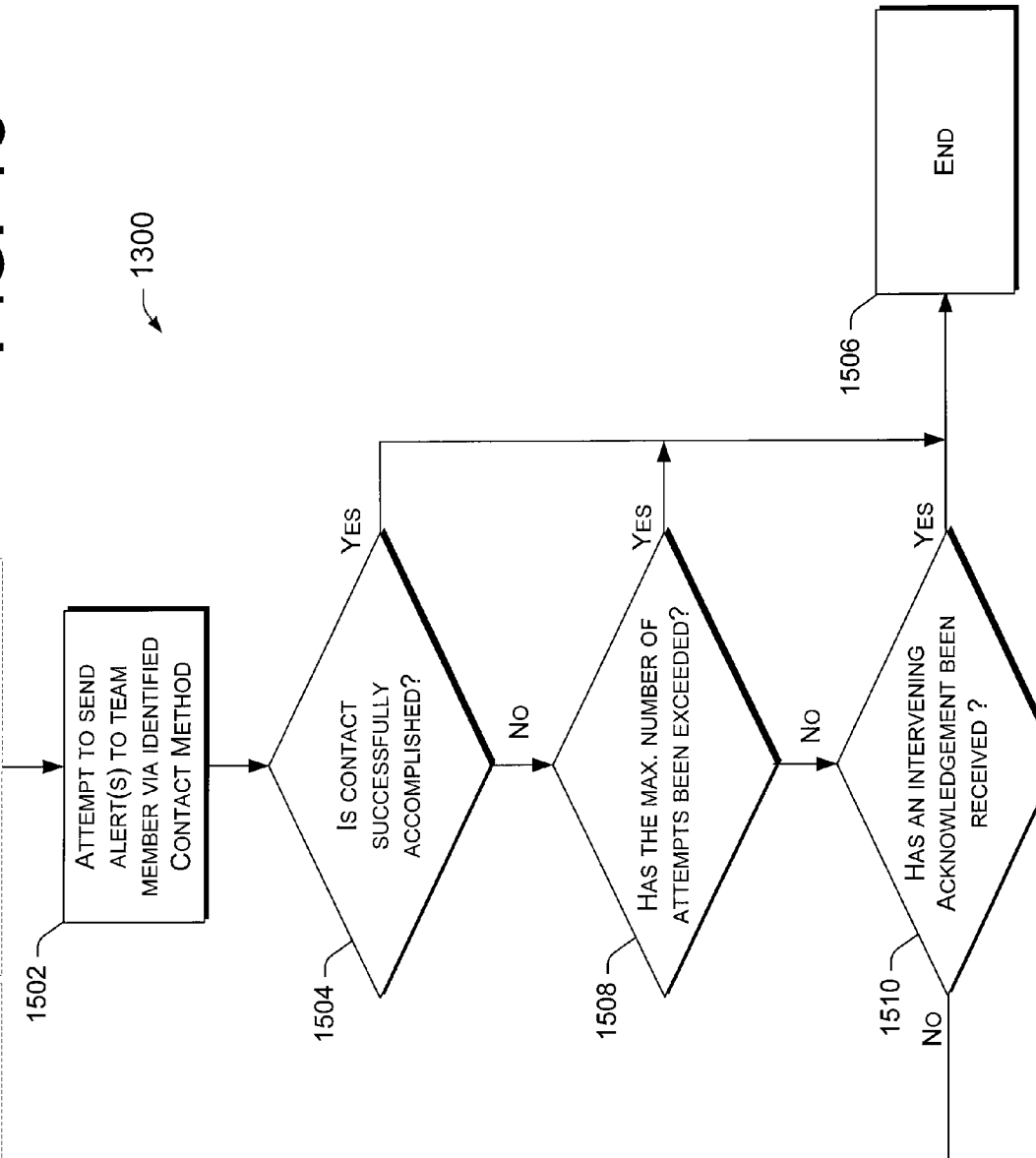

IMPLANTABLE MEDICAL DEVICE ALERT MANAGEMENT

FIELD OF THE INVENTION

The subject matter presented herein generally pertains to implantable medical devices (IMDs) and external medical devices configurable to communicate with the IMDs and specifically relates to managing IMD-related alerts.

BACKGROUND

Various implantable medical devices (IMDs) exist in the marketplace to treat a range of patient conditions. For example, IMDs are utilized to address cardiac-related conditions. In many instances IMDs are configured to communicate with external medical devices. Alerts relating to the IMDs can be generated by the IMD and/or by the external devices. Traditionally all IMD-related alerts are sent to a particular medical worker who determines how to handle the alerts.

SUMMARY

Exemplary systems and methods for automatically managing implantable medical device (IMD) related alerts are described. One method generates a user interface that allows a user to define a set of parameters relating to managing implantable medical device related alerts. The method also receives user-input that defines the values.

Another method receives implantable medical device-related alerts. The method automatically manages the implantable medical device alerts by parsing the alerts through a set of predefined parameters.

BRIEF DESCRIPTION OF THE DRAWINGS

Features and advantages of the described implementations can be more readily understood by reference to the following description taken in conjunction with the accompanying drawings. In the description that follows, like numerals or reference designators will be used to reference like parts or elements wherever feasible.

FIGS. 13-15 show a flowchart of an exemplary method for managing IMD-related alerts in accordance with some implementations.

DETAILED DESCRIPTION

Overview

Various exemplary techniques, methods, devices, systems, etc., described herein pertain to automated alert management for implantable medical devices (IMDs). An increasing number of different IMD-related alerts are being developed as IMD and/or system capabilities improve. For instance, IMDs offer ever increasing capabilities of sensing and/or treating patients. The processing power of the IMD and/or the other system devices can allow more types of IMD-related alerts to be generated and the ease of communication between system components allows the IMD-related alerts to be generated and/or transmitted more often.

The IMD-related alerts can pertain to any item of interest associated with patient care. For instance, IMD-related alerts can relate to a sensed patient condition, a functionality of the IMD, an interruption in communication between system devices and the like. IMD-related alerts can be generated by an IMD and/or by other system devices. For instance, a low battery alert can be generated by the IMD while a "no data received from the IMD" alert can be generated by an external device, such as a transmitter or device manager.

The inventive concepts offer automated techniques for managing the IMD-related alerts. For example, the automated techniques can utilize a set of predefined parameters that specify how IMD-related alerts should be handled. For instance, the predefined parameters can relate to who should receive IMD-related alerts, when the IMD-related alerts should be delivered, and a delivery mechanism for the IMD-related alerts among others. The inventive techniques can be applied broadly, yet are customizable where desired. As a result, a relatively small number of predefined parameters can be utilized to manage a relatively high number of different IMD-related alerts.

First Exemplary System

Figure 1:
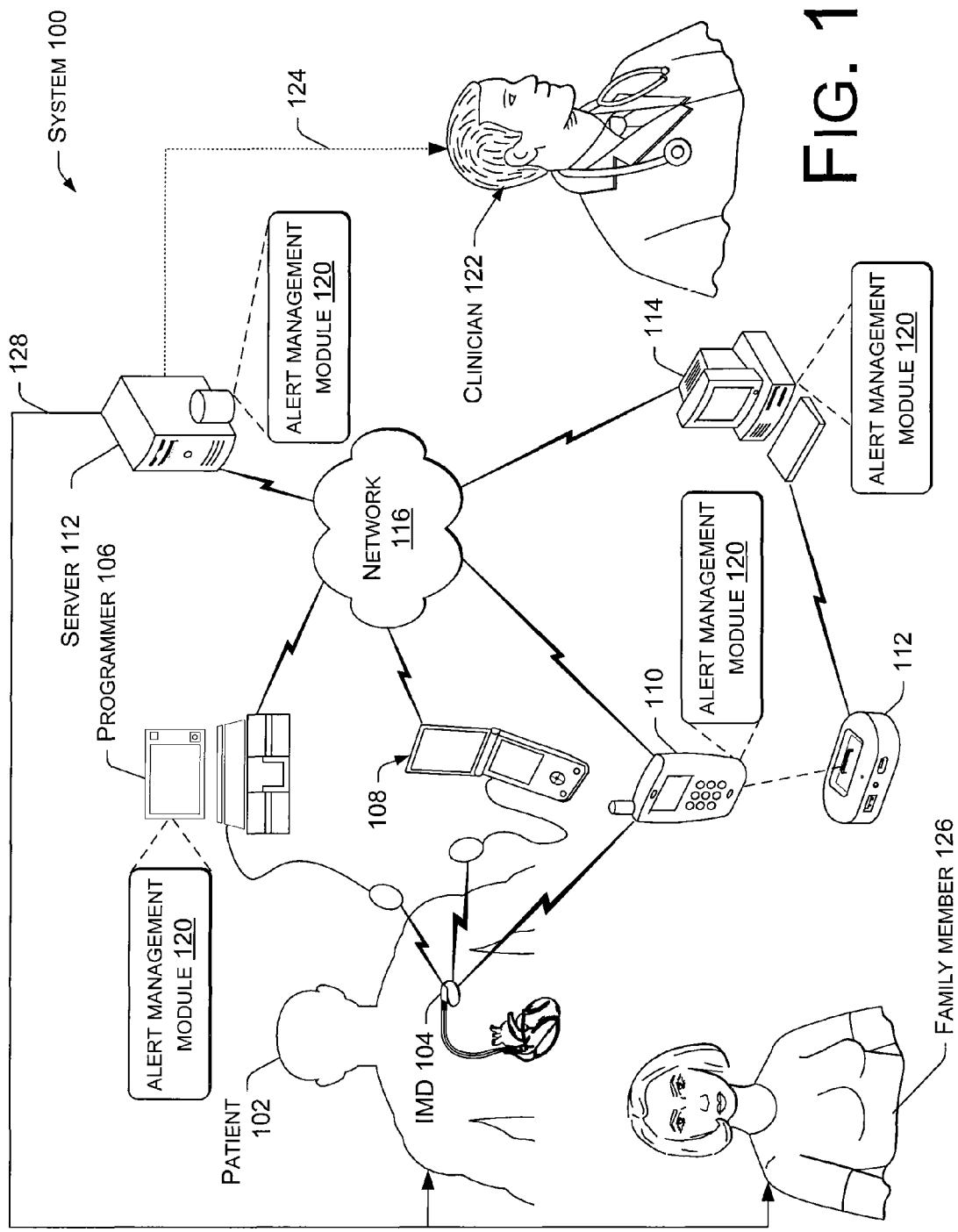
FIGS. 1 and 9 show system diagrams that illustrate exemplary configurations for managing IMD-related alerts in accordance with some implementations.

FIG. 1 illustrates a system 100 that can provide automated management of implantable medical device (IMD)-related alerts. System 100 includes a patient 102 that has an implanted IMD 104. The IMD is configured to communicate with various external medical devices including, for example, a programmer 106, a device manager 108, and/or a transmitter 110. The programmer, device manager, and/or transmitter can be configured to communicate with one another and/or with other external system devices including a server 112 and a personal computer 114. Inter-device communication can be accomplished via a network 116. The network can utilize various wired and/or wireless technologies. While a single network is illustrated, network 116 can include multiple networks including the internet and/or other technologies. Security techniques can be employed on network 116 and/or on the connected devices to safeguard patient information.

IMD-related alerts can be generated by any system device. For instance, IMD 102 can generate an IMD-related alert that the patient is experiencing ventricular fibrillation. In another example, transmitter 110 can generate an IMD-related alert that the transmitter has not received data from the IMD in a specified period of time. One or more system devices can include an alert management module 120 to handle the IMD-related alerts. In the illustrated configuration programmer 106, transmitter 110, server 112, and personal computer 114 include alert management modules 120. Alternatively or additionally, IMD 104 and device manager 108 can include alert management modules 120.

In this case, alert management modules 120 utilize various parameter objects to accomplish IMD-related alert management. Briefly, the parameter objects are populated with parameters that are defined prior to receipt of IMD-related alerts. The predefined parameter objects serve to determine how particular IMD-related alerts are handled. For instance, a first parameter object can relate to who should receive an individual IMD-related alert. Parameter objects are described in more detail below in relation to FIG. 2.

In some cases IMD-related alerts can be sent to a clinician 122 as indicated at 124 and/or sent to a family member 126 of the patient 102 as indicated at 128. The predefined alert management modules 120 utilize a relatively small number of parameter objects to handle a multitude (and potentially all) IMD-related alerts that may be generated by system 120. The alert management modules 120 allow instructions for handling various IMD-related alerts to be established in an efficient yet customizable manner. For example, an alert management module can include predefined parameter objects to handle all IMDs of a particular type (or multiple types) encompassed by the system or a subset of the system. For instance, an alert management module could handle a single model or multiple models of IMDs. In other cases, alert management modules 120 can be customized as desired. In one case, clinical groups and/or individual clinicians can predefine how their IMD-related alerts are to be managed via the alert management module. In other cases, IMD-related alerts for individual patients can be managed as desired by for instance, a clinical group, a clinician and/or the patient.

While the illustrated implementation includes alert management modules functioning on individual system devices, other implementations can utilize a web-based or distributed approach. For instance, in a web-based approach more of the alert management processing can be performed at a central location, such as server 112, with the remaining devices acting as thin-clients that perform a user input/output role.

Exemplary Parameter Objects

Figure 2:
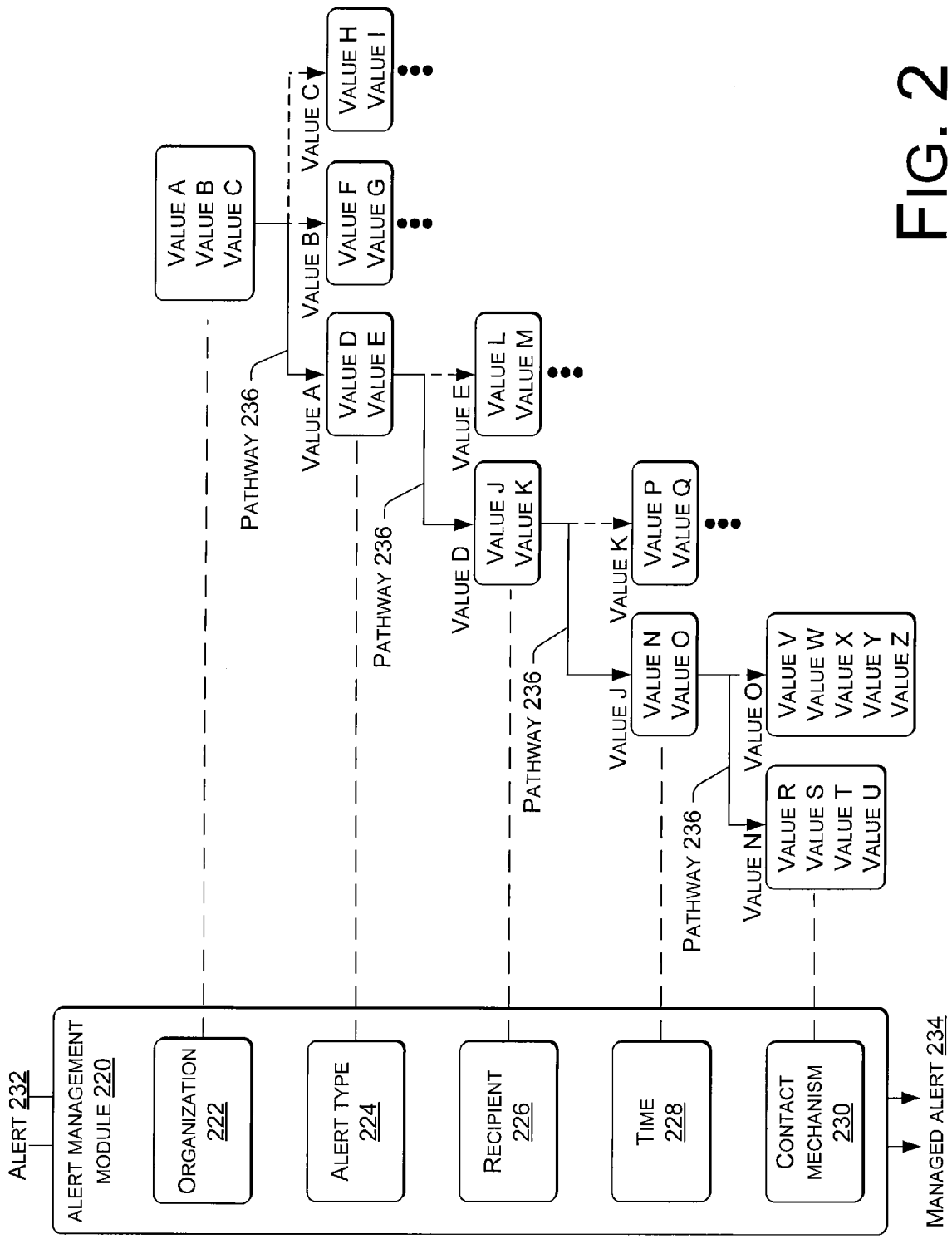
FIG. 2 shows a component for managing IMD-related alerts that is included in the systems of FIGS. 1 and 9 in more detail in accordance with some implementations.

FIGS. 2-8 provide an example where parameter objects are predefined to automatically manage IMD-related alerts. FIG. 2 shows an alert management module that includes multiple pre-definable parameter objects. FIGS. 3-8 show examples of how the alert management module's parameter objects can be predefined. In various examples, an exemplary method can include generating a user interface using a computing device (e.g., a device with one or more processors and associated memory) where the generated user interface allows a user to enter or select values for a set of parameters (e.g., to define the set) where the set of parameters relates to managing different implantable medical device related alerts. Upon generation, a clinician can then enter, via the user interface, values that define the set of parameters.

FIG. 2 shows a more detailed view of alert management module 120 that includes multiple parameter objects on the left side of the physical page upon which the FIGURE appears. Corresponding predefined parameter values of the parameter objects are shown in a cascading manner on the right side of the page. The parameter objects are cascading in that parameter values defined for the parameters toward the top of the page can affect the parameter values of the subsequent or underlying parameters. Assume for purposes of explanation that process flow for automated alert management proceeds from the top of the page on which FIG. 2 appears to the bottom of the page. In this specific instance the predefined alert management module includes five parameter objects: an organization parameter object 222; an alert type parameter object 224; a time parameter object 226; a recipient parameter object 228, and a delivery mechanism parameter object 230. Though five parameter objects are illustrated in this implementation, more or less parameter objects can be employed in other configurations as should become apparent to the skilled artisan. Further, as should become apparent from the description below, other and/or different parameter objects can be utilized.

For each parameter object 222-230 one or more parameter values is defined on the right portion of the page. Due to space constraints, the parameter values are represented by alphabetic designators on FIG. 2. More concrete examples of parameter values are described below in relation to FIGS. 3-8. In relation to organization parameter object 222, the predefined parameter values are "A", "B", and "C". Subsequent parameter objects can include predefined parameter values relative to the parameter values of each of the preceding parameter objects. For instance, for alert type parameter object 224 the predefined parameter objects relating to value "A" are value "D" and value "E". Similarly the predefined parameter objects relating to value "B" are "F" and "G" and the predefined parameter objects relating to value "C" are "H" and "I". For sake of brevity not all portions of the FIGURE are followed to completion. Instead, areas which are intentionally left incomplete are indicated by three vertically arranged circles. The parameter objects are cascading in that for example, by defining three parameter values (A, B, and C) for organization parameter object 222 then each of those three parameter values can be separately addressed for the alert type parameter object 224. Similar relationships can be followed through the process flow.

An IMD-related alert 232 received by the alert management module 220 can be managed by cascading the alert through the predefined values of the parameter objects to produce a managed IMD-related alert 234. The term managed IMD-related alert 234 does not necessarily imply that the alert is somehow changed, instead the alert is managed in that actions, such as delivering the alert are taken in accordance with the predefined parameter values. For instance, a received IMD-related alert that fell within the predefined value "A" for the organization parameter object 222, value "D" for the alert type parameter object 224, value "J" for the recipient parameter object 226, value "N" for the time parameter object 228, and value R for the contact mechanism parameter object 230 that collectively define a cascading management path 236 that is indicated generally as bold continuous lines. (Individual portions of the cascading management path are identified in FIG. 2).

The received alert can be handled in accordance with the parameter values of the cascading management path 236. For example, the IMD-related alert would be delivered to a recipient defined in the recipient parameter object 226 via a contact mechanism defined in the contact mechanism parameter object 230 dependent upon the time that the alert was received relative to defined time parameter object 226. In summary, the predefined parameter values in each of the multiple parameter objects allow a large number of different IMD-related alerts to be automatically managed in accordance with the predefined values.

Described another way, the defined parameters 222-230 can be thought of as a set of generic parameters. The set of parameters are generic in that they can be utilized to manage a plurality of IMD-related alerts. When an individual IMD-related alert is parsed through the set of parameters a management path is defined for handling the alert. Such a configuration allows a relatively small number (i.e., five in the illustrated implementation) parameters to be defined to manage a relatively large number (i.e., potentially hundreds) of different alerts. Accordingly, at least some of the present implementations can offer an order of magnitude of saving to the user relative to the number of alerts that can be automatically managed versus the number of parameters defined by the user.

FIGS. 3-8 show graphical user-interface (GUIs) or screenshots that allow parameter objects to be predefined or otherwise configured for managing IMD-related alerts. Assume for purposes of explanation that the screenshots are generated for an electro physiologist (EP) who wants to configure his/ her automated alert management system. Among other configurations, the screenshots can be generated on programmer 106 or personal computer 116 as illustrated in FIG. 1. To mimic an actual usage scenario a finger image of the EP is shown superimposed over some of the screen shots described below. The finger image is included for purposes of explanation and is not intended to be part of the screen shot.

For sake of brevity only one screen shot relative to a given parameter is illustrated in this discussion. The skilled artisan should recognize from the discussion relating to FIG. 2 that multiple similar screenshots may be employed for a given parameter as determined by the parameter values defined for the preceding parameters.

Figure 3:
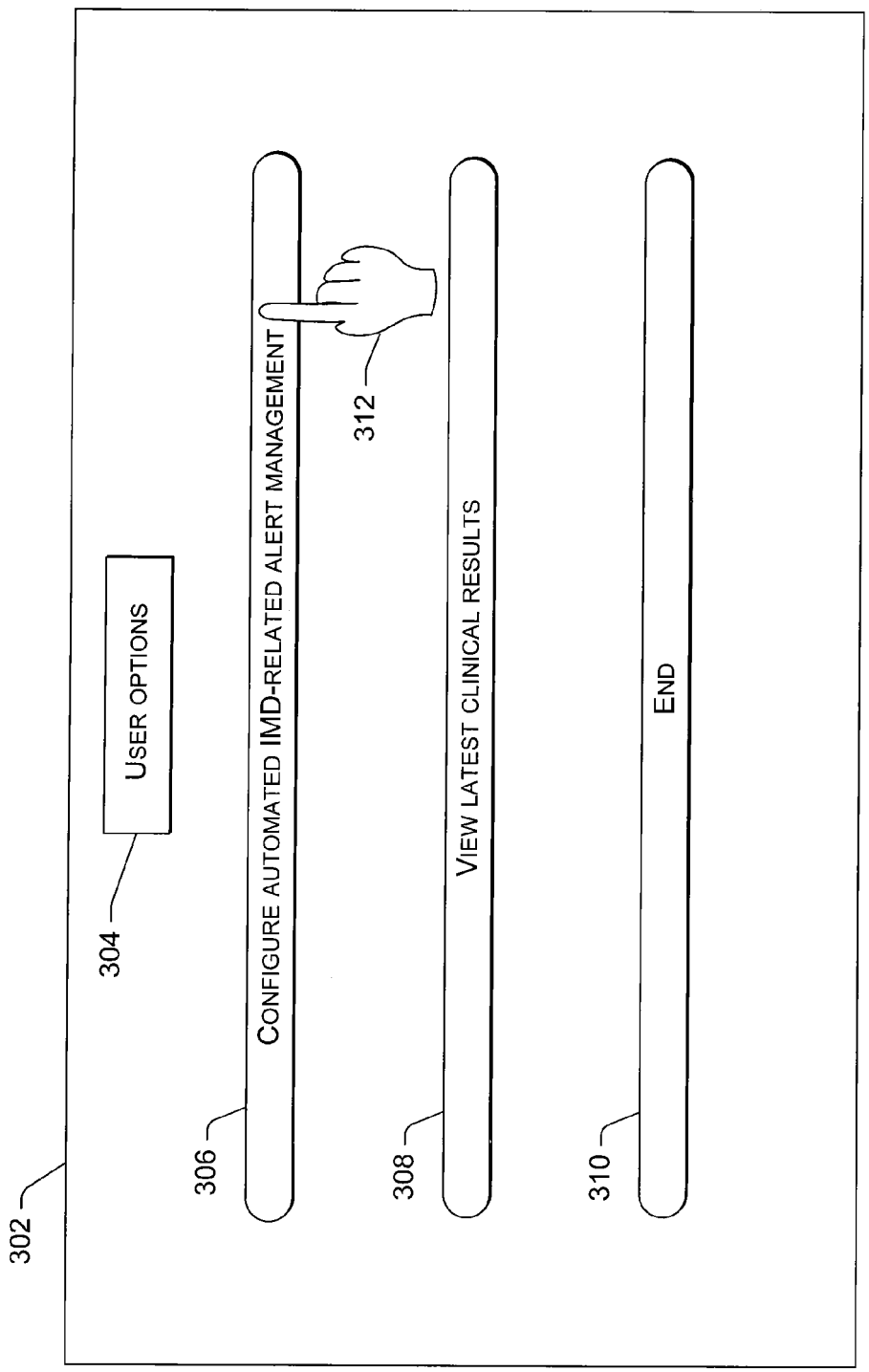
FIGS. 3-8 show screenshots for managing IMD-related alerts in accordance with some implementations.

FIG. 3 shows a screenshot 302 that lists various user-selectable options 304 for the user (in this case the EP). In this scenario the user-selectable options include a "configure automated IMD-related alert management" dialog box 306, a "view latest clinical results" dialog box 308, and an "end" dialog box 310. Assume for purposes of explanation that the EP selects the "configure automated IMD-related alert management" dialog box 306 as indicated generally at 312.

Figure 4:
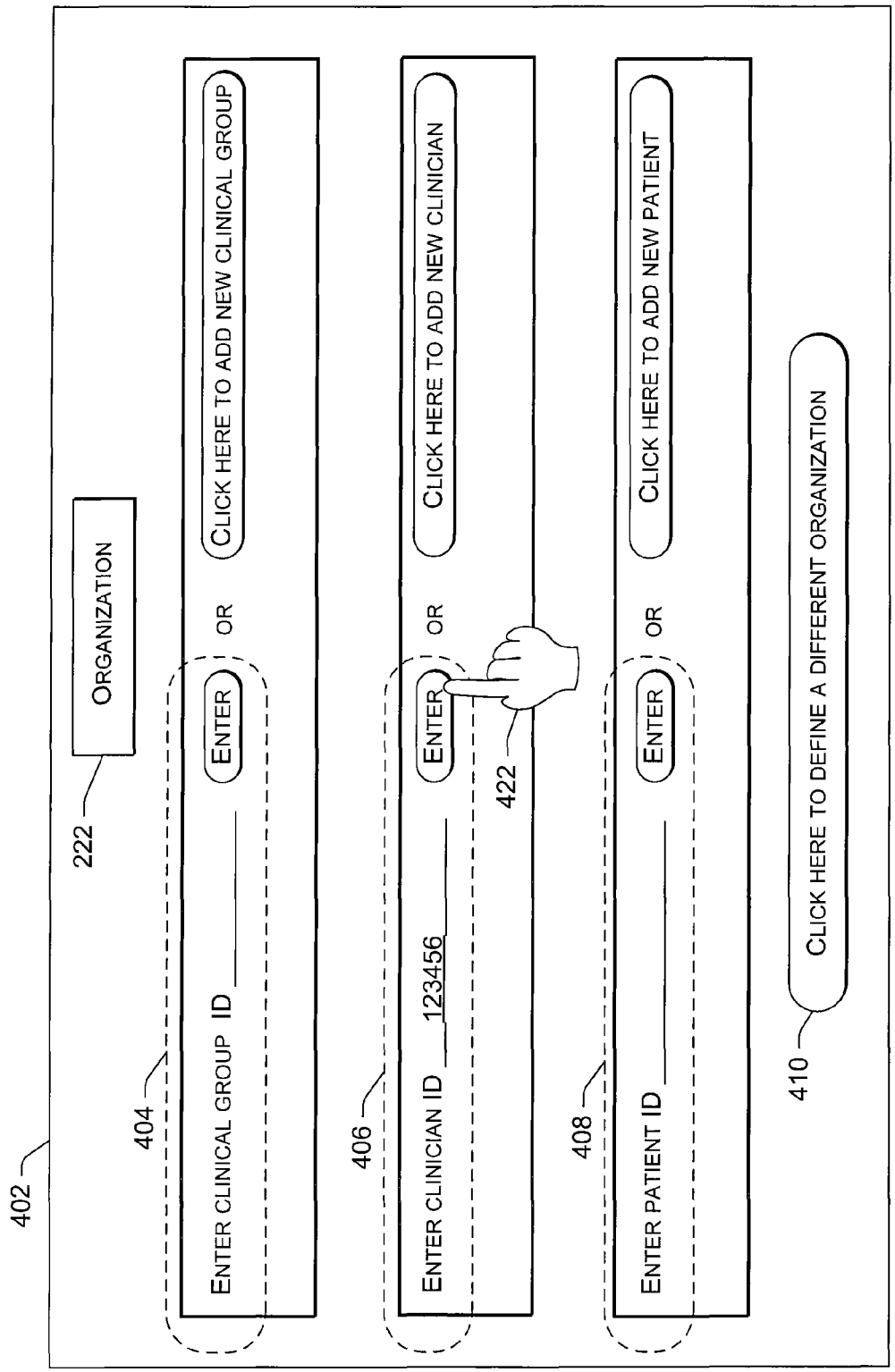

FIG. 4 shows a screenshot 402 generated responsive to the user selection described above in relation to FIG. 3. FIG. 4 relates to the organization parameter object 222 introduced above in relation to FIG. 2. Screenshot 402 allows the EP to predefine organization parameter object 222. In this case three organizational categories or groups are available to the user. As indicated at 404 the EP can organize IMD-related alerts relative to a clinical group. As indicated at 406, the EP can organize the IMD-related alerts relative to a clinician or relative to a patient as indicated at 408. The EP can also define a different organizational category as indicated at 410. In some cases the EP can utilize more than one organizational category. For example, the EP may belong to a clinical group of multiple EPs and organize IMD-related parameter alerts based upon the clinical group. The EP can then also organize based upon any exceptions that the EP may want for himself/herself relative to the clinical group and/or the EP may want to organize the IMD-related alerts for a specific patient. In this instance, assume that the EP is a sole practitioner and has entered his/her clinician ID of "123456" at 406 and selected "enter" at 422. The clinician ID can be utilized to associate the EP with his/her information in the system. The system information may be utilized to pre-populate various fields while the EP is configuring the automated alert management system.

Figure 5:
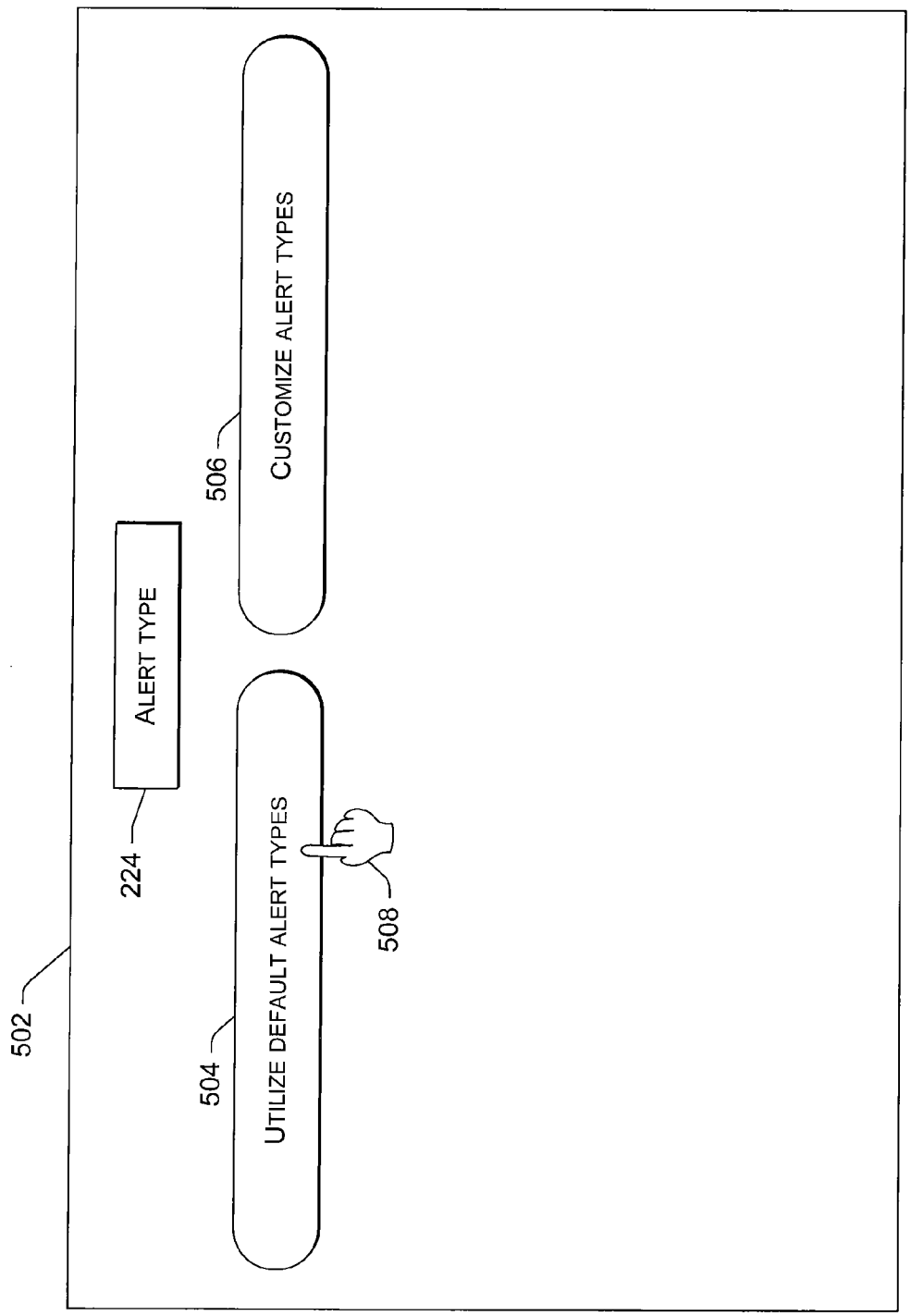

FIG. 5 shows a screenshot 502 generated upon the user selection of FIG. 4. Screenshot 502 relates to the alert type parameter object 224 introduced in relation to FIG. 2. In this case two options are provided. User-selectable box 504 allows the EP to "utilize default alert types". User selectable box 506 allows the EP to "customize alert types" for other than the default alert types. The default alert types can be established for the automated alert management system by various parties. For instance, a provider or manufacturer of IMDs can establish the default alert types.

Alert types can be specified based upon various classification criteria. For example, one alert hypothetical classification scheme includes three alert types: type 1 or urgent, type 2 or important, and type 3 or procedural. The urgent type (1) includes time-critical IMD-related alerts such as the patient is experiencing ventricular fibrillation. The important type (2) includes IMD-related alerts that require notice but not immediate attention, such as a low IMD battery alert. The procedural type (3) includes IMD-related alerts that can relate to patient management. For instance, one example of a patient management IMD-related alert can be an interference alert that indicates that transmissions between the IMD and the transmitter are experiencing interference. Such an alert may indicate that the patient should schedule an appointment to see if the IMD can be tuned to a clearer frequency. If the EP is not satisfied with the default IMD-related alert types the EP can customize the alert types via dialog box 506. Assume that in this instance, the EP selects the default alert types as indicated generally at 508.

Figure 6:
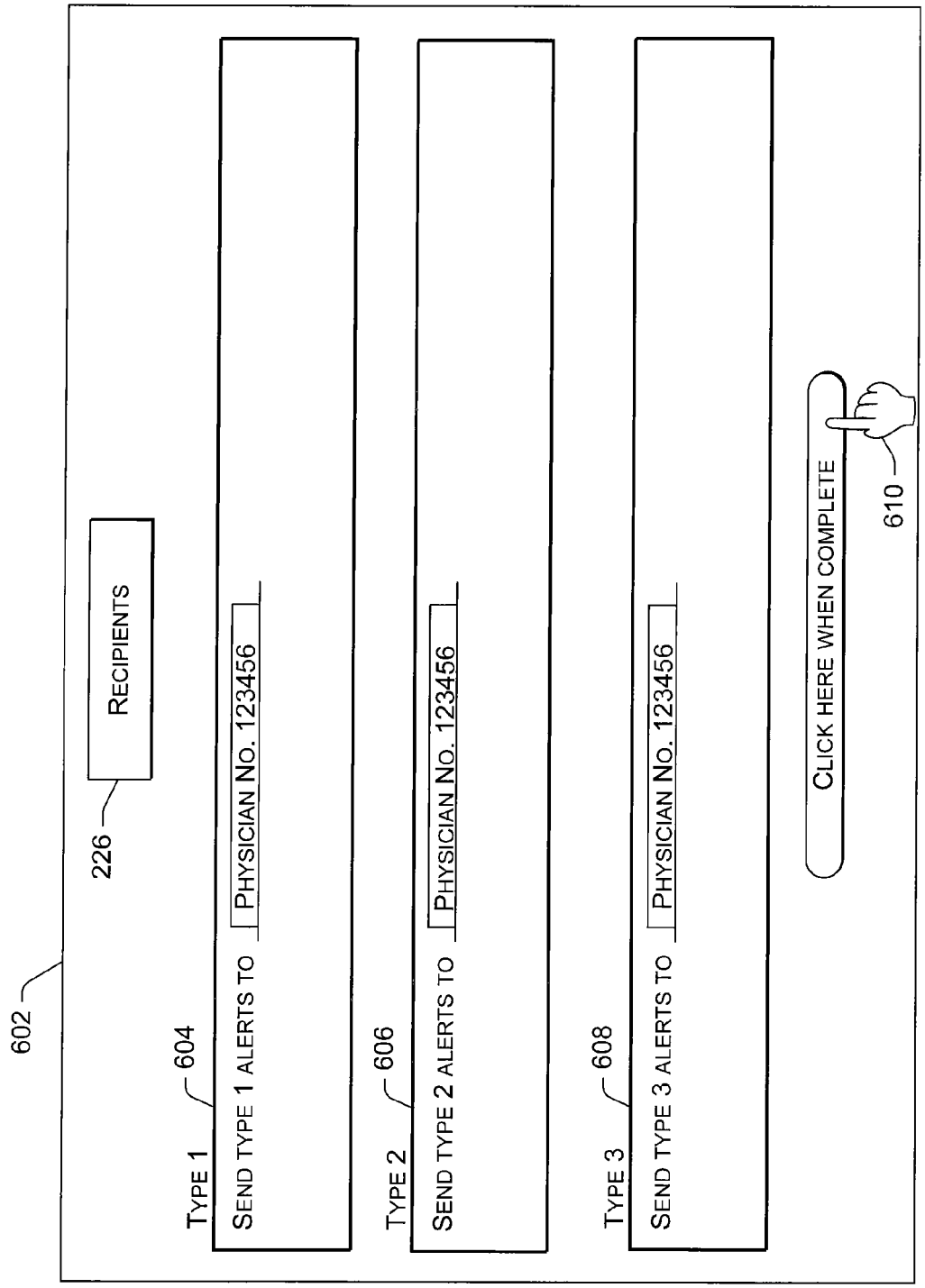

FIG. 6 shows a screenshot 602 relating to defining the recipient parameter object 226 introduced in relation to FIG. 2. In this case recipient(s) for each IMD-related alert type specified in FIG. 5 can be specified independently of the other alert types. A type 1 IMD-related alert window 604 allows the EP to select recipients for type 1 alerts. Similarly, a type 2 alert window 606 and a type 3 alert window 608 allow the EP to select recipients for type 2 and type 3 IMD-related alerts respectively. In this case the EP's ID number is pre-populated into each of window 604-608 to aid the EP in defining the parameter. The EP can supplant the pre-populated content with his/her own content as desired. For instance, the specified recipient can be one or more of the EP, the patient's cardiologist, the patient's internist, the patient, the patient's in-home care provider, the patient's relative or friends etc. Assume for purposes of explanation that the EP is satisfied with the content defined for the recipient parameter object and selects to move to the next parameter object as indicated generally at 610.

Figure 7:
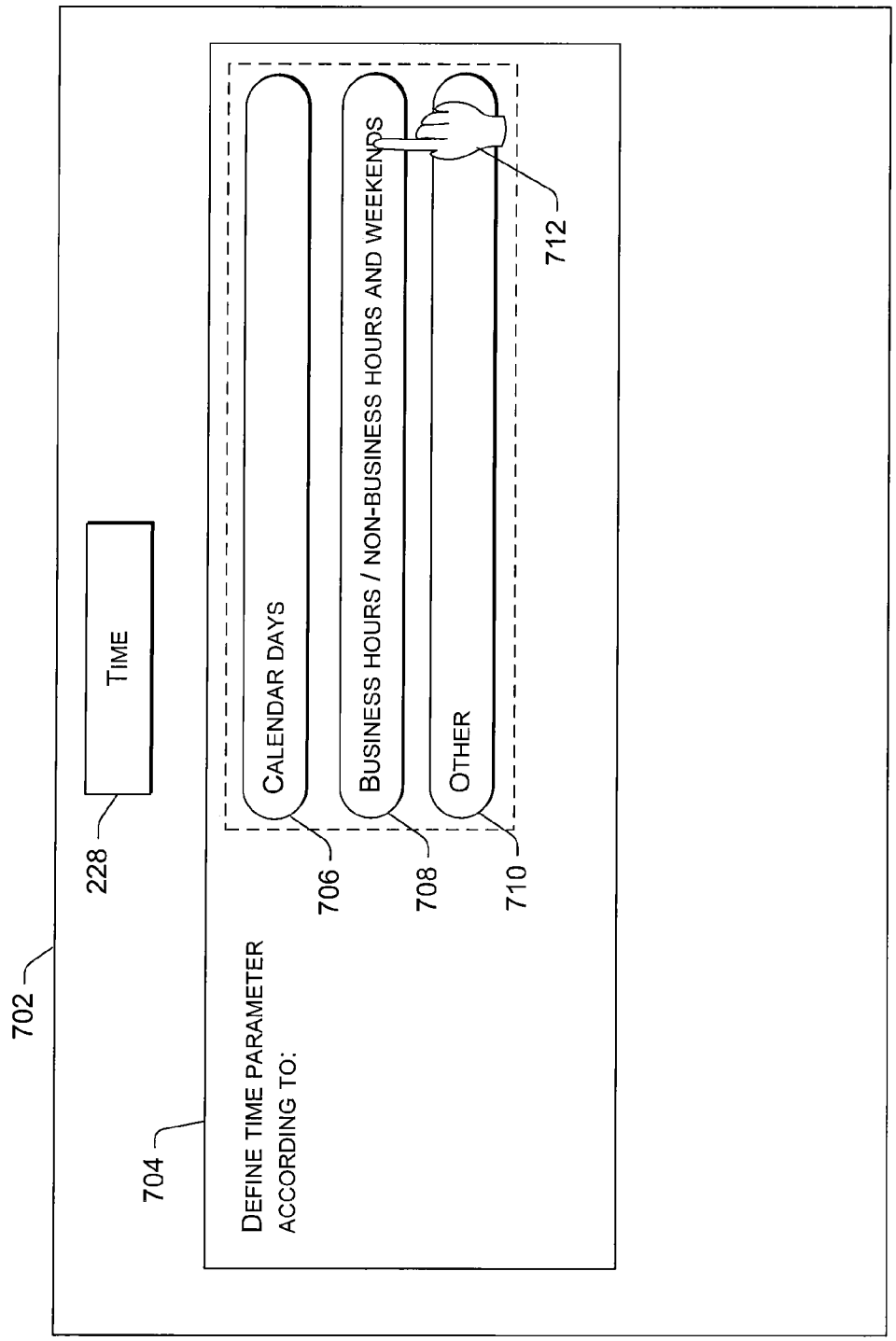

FIG. 7 shows screenshot 702 relating to defining the time parameter object 228 introduced in relation to FIG. 2. Screenshot 702 includes a window 704 in which the EP can define how time is categorized in the automated IMD-related management process. Window 704 allows the EP to categorize time based upon "calendar days" as indicated at 706, as "business hours/non-business hours and weekends" at 708. Further, the EP can define his/her own other time categorization as indicated at 710. The calendar day categorization allows the EP to adjust IMD-related alert management based upon specific days that individual IMD-related alerts are received. For instance, the EP can distinguish normal work weeks from vacation weeks among others as desired. The business hours/non-business hours categorization allows the EP to specify how IMD-related alerts are handled during his/her normal business hours and a different way that the IMD-related alerts are handled during other (non-business hours). Assume that in this instance the EP selects the business hours/non-business hours categorization as indicated at 712. In some instances, the time parameter object can allow the EP to specify the time parameter in different ways for different alert types and/or for different recipients among others.

Figure 8:
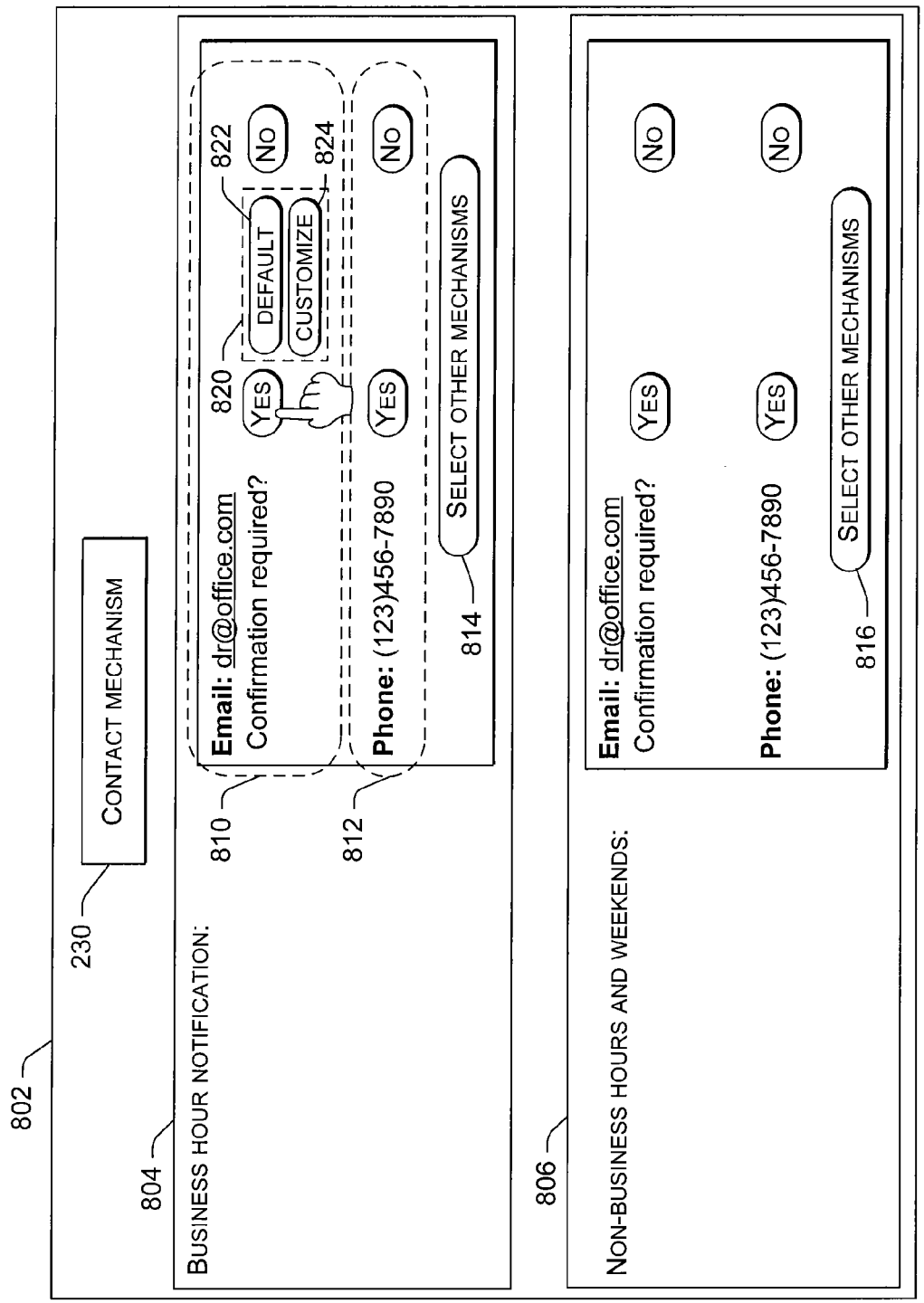

FIG. 8 shows a screenshot 802 relating to defining the contact mechanism(s) parameter object 230 introduced in relation to FIG. 2. In this case the screenshot includes a business hour notification window 804 and a non-business hour notification window 806. Recall that the EP defined the time parameter object in relation to FIG. 7 into these two categories (i.e., business hours versus non-business hours). In this case, both windows 804, 806 are pre-populated with the EP's information. For example an email field 810 of window 804 is populated with the EP's email address "dr@office.com". Similarly, a phone field 812 is populated with the EP's telephone number "(123)456-7890". While email and telephone mechanisms are detailed here, any combination of delivery mechanisms can be utilized. Further, a patient may list one or more friends or family members as contacts with associated contact information. Examples of other delivery mechanisms can include faxes, pages, short message service (SMS), and interactive voice recording (IVR), among others. For example, a patient may elect to receive an alert via a device manager and via a cell phone (see, e.g., the device manager 108 and the transmitter 110 of FIG. 1). In this example, the cell phone may notify the patient of the alert condition before data is sent from the device manager (e.g., sent via a network).

The EP can select other mechanisms at 814 and 816 for windows 804, 806 respectively. Further, while in this instance the delivery mechanisms are the same for business hours and non-business hours, the EP can easily customize the delivery mechanisms in either or both cases. For instance, the EP may want his/her office phone number called during business hours, but his/her cell phone called at non-business hours.

In relation to IVR additional screenshots can be generated which allow the EP to specify the words contained in the message or to select a default message. Further, the EP can be allowed to generate the message in his/her own voice if desired. Messages conveyed in the EP's voice may be more positively received by the patient or the patient's family/friends than messages conveyed by a generic voice. This feature also allows for communication in obscure languages and accents.

Screenshot 802 further offers the EP an opportunity to specify whether confirmation is required that the IMD-related alert was received by the intended recipient. For instance, in relation to email field 810 the screenshot offers the EP the option of specifying "yes" that confirmation is required or "no" that confirmation is not required. In this instance the EP positions his/her finger over the "yes" dialog box as indicated at 820. Responsively, a drop down menu is generated that allows the EP to select either default confirmation as indicated at 822 or to select to customize the confirmation as indicated at 824. The skilled artisan should recognize various confirmation schemes. In one example, the default condition may require a reply email indicating that the email had been read.

If the EP is concerned that others may open his/her email and he may not become aware of the email then the EP can request that the reply email contain the EP's ID number. In this example, the EP specified in relation to FIG. 6 that all three types of IMD-related alerts are sent to the EP. In implementations where different recipients are specified the delivery mechanism screenshot can allow different contact mechanisms to be specified for different recipients. Further, the confirmation can be different. For instance, consider a case where the EP directs a type of alert to the patient. The EP can specify IVR as the contact mechanism. In the IVR the EP can request that the patient enter the last four digits of their social security number to confirm that the IVR message is in fact reaching the intended recipient.

The screenshots illustrated in relation to FIGS. 3-8 offer but one example for predefining the parameter objects utilized by the alert management module to handle IMD-related alerts. The alert management module then automatically manages any IMD-related alert in accordance with the predefined parameter objects. Through the parameter objects, the alert management module offers alert management that is both generic and customizable as desired. The alert management module readily accepts new patients, organizations or reorganizations, clinicians etc. Further, the parameter objects are readily updated to reflect new clinical studies for best patient practices. Further, as technology advances the alert management module can be readily adapted to include new and/or different parameter objects to automatically manage IMD-related alerts.

Second Exemplary System

Figure 9:
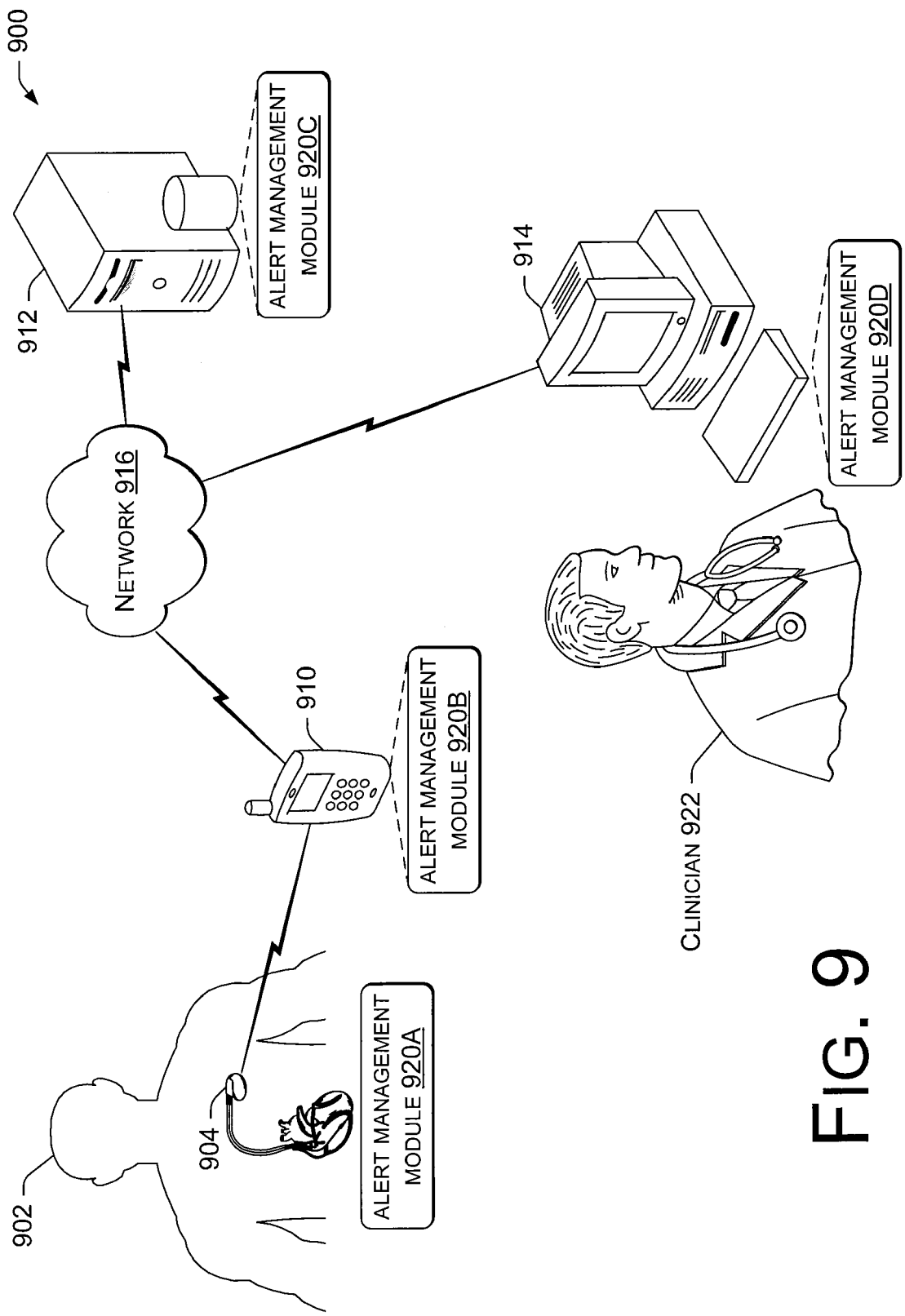

FIG. 9 shows a system 900 configured to automatically manage IMD-related alerts. System 900 includes a patient 902 that has an implanted IMD 904. The IMD 904 can communicate with a transmitter 910 (e.g., an at-home unit, a mobile unit, a cell phone with appropriate RF communication circuitry, etc.). The transmitter 910 can connect to various other system devices such as server 912 and personal computer 914 via network 916 (e.g., via analog, cellular, WiFi, WiMax, etc.). In this case, each system device includes an alert management module to handle alert-related tasks. IMD 904 includes alert management module 920A, transmitter 910 includes alert management module 920B, server 912 includes alert management module 920C, and personal computer 914 includes alert management module 920D.

While in this case each system device includes an alert management module the functional capabilities of the various alert management modules is not necessarily identical. For example, alert management module 920D associated with personal computer 914 can include mechanisms to generate screenshots, such as those described in relation to FIGS. 3-8 that allow a clinician 922 to predefine alert management parameters. In contrast, the alert management modules 920A, 920B of the IMD and the transmitter respectively can have reduced and/or different functionality relative to alert management module 920D. For example, consider a hypothetical scenario where the clinician 922 defines two types of IMD-related alerts via screenshots generated on personal computer 914. Assume further, that the clinician defines that IMD-related alerts of the first type are to be handled immediately, while IMD-related alerts of the second type can be delayed by up to two hours. In such a case, the IMD's alert management module 920A can be programmed to reflect the defined alert management configuration. Then whenever the IMD generates an IMD-related alert the alert management module 920A can determine the type of the alert.

In the case of a type 1 IMD-related alert, the alert management module 920A can attempt to transmit the alert to transmitter 910 as quickly as possible. In the case of a type 2 IMD-related alert, the alert management module 920A can potentially delay sending the alert to the transmitter until the next scheduled transmission time. Communications between IMD 904 and transmitter 910 use IMD power resources. Delaying transmission until the scheduled transmission time can allow the IMD-related alert to be transmitted with other data thereby potentially saving IMD power resources. Accordingly, whether the IMD's alert management module 920A should provide more robust or more limited functionality can include considerations such as the processing, memory, and/or power resources available on the IMD, among other considerations.

Similar considerations to those mentioned above in relation to the IMD's alert management module 920A can also be applicable to the transmitter's alert management module 920B. For instance, if the transmitter receives an IMD-related alert from the IMD, the alert management module 920B can determine whether to attempt to send the alert to the server immediately or within a predefined time period. In a further example, the transmitter may generate the IMD-related alert and then the transmitter's alert management module can determine an appropriate response. In one such hypothetical case, assume that the transmitter is scheduled to receive data from IMD 920A every two hours, but has not received data for three hours. The transmitter can responsively generate a "no-contact" IMD-related alert. The transmitter's alert management module can determine how to handle the IMD-related alert. For instance, continuing with the above example, the no-contact IMD-related alert may be a type 1 alert and therefore the alert management module sends the alert immediately.

In some configurations, not all system devices include an alert management module. For example, the illustrated configuration could be employed with an IMD that did not include any alert management functionality. In still other configurations, the alert management techniques can be web-based. In web-based configurations some or all of the alert management functionality occurs on a remote device such as server 912. In such a scenario, local devices, such as personal computer 914 can have a less robust alert management module or may not have a resident alert management module. Instead, the local device acts more like an input/output device on behalf of the remote device upon which processing for alert management largely occurs. The clinician and/or patient may not readily discern what system configuration is performing the alert management functionality.

Exemplary Implantable Medical Device

Figure 10:
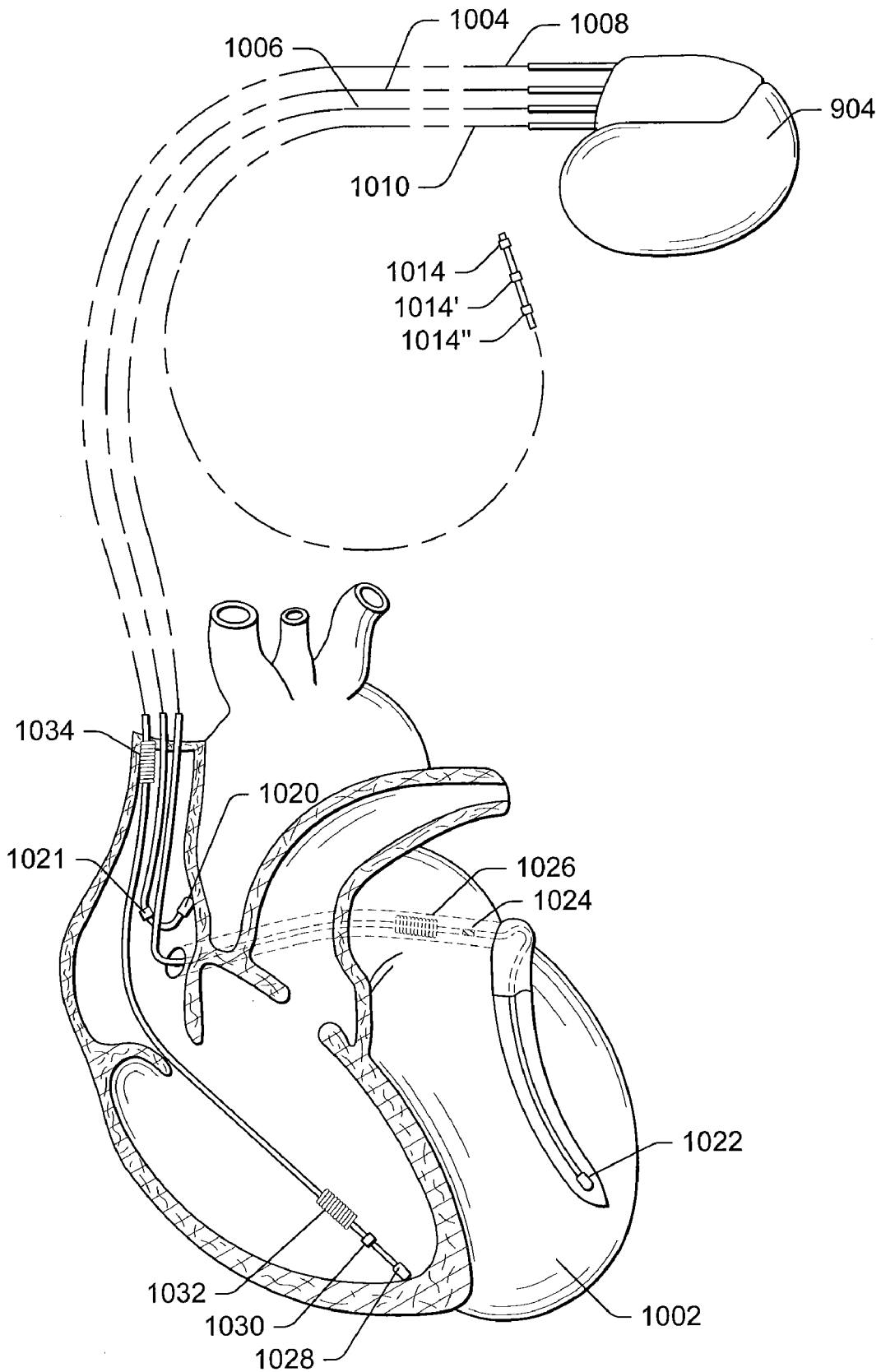
FIGS. 10-11 show an exemplary IMD configured to manage IMD related alerts in accordance with some implementations.
Figure 11:
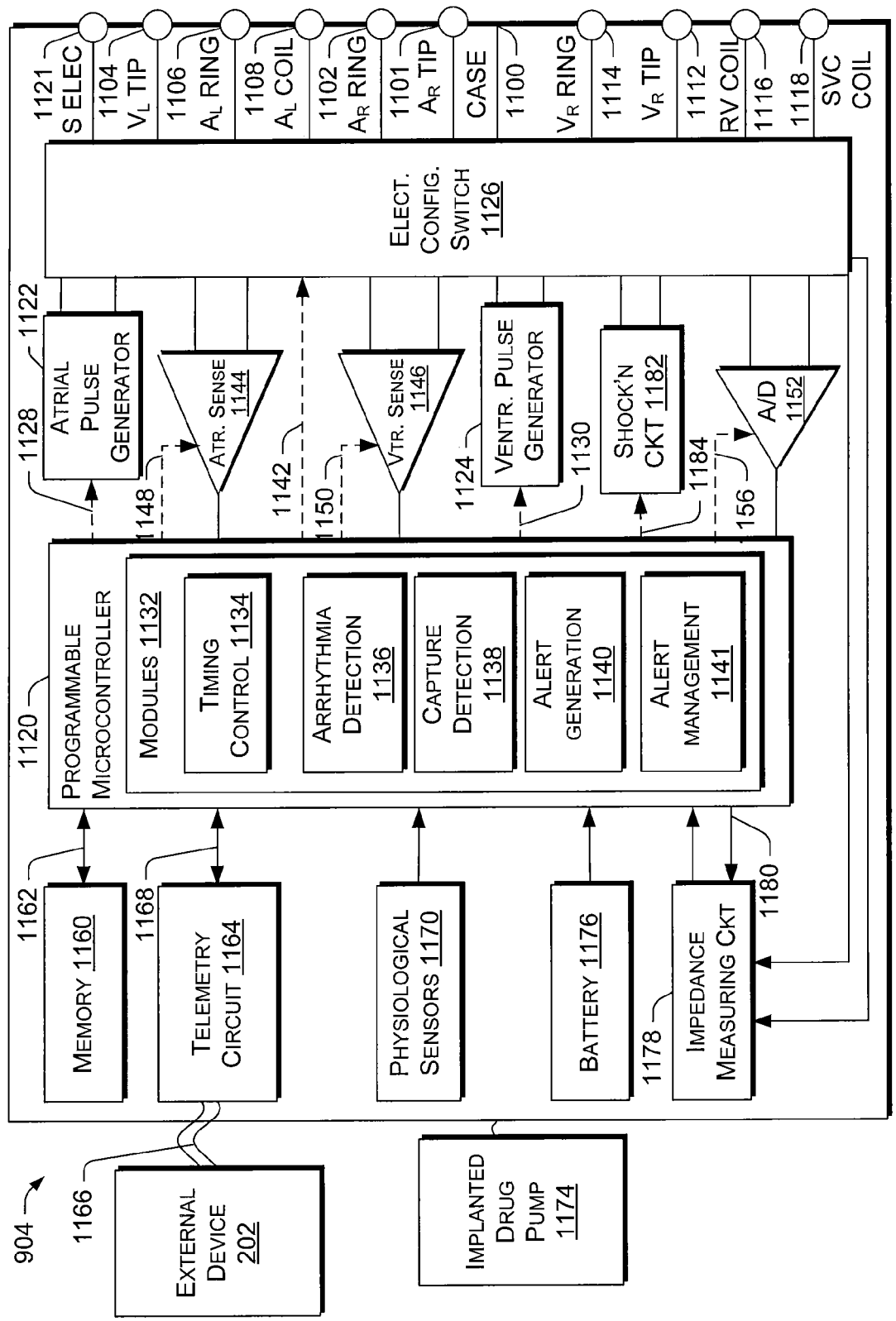

The techniques described above and below can be implemented in connection with any IMD that is configured or configurable to sense or otherwise gather biological data from a patient. FIGS. 10-11 describe an IMD in the form of an implantable cardiac device (ICD) for sensing cardiac data and/or providing cardiac therapy. The principles described in relation to a cardiac device are equally applicable to other device configurations.

FIG. 10 shows an exemplary IMD 904 in electrical communication with a patient's heart 1002 by way of three leads 1004, 1006, 1008, suitable for delivering multi-chamber stimulation and shock therapy. The leads 1004, 1006, and 1008 are optionally configurable for delivery of stimulation pulses suitable for stimulation of autonomic nerves, non-myocardial tissue, other nerves, etc. In addition, IMD 904 includes a fourth lead 1010 having, in this implementation, three electrodes 1014, 1014', 1014" suitable for stimulation and/or sensing of autonomic nerves, non-myocardial tissue, other nerves, etc. For example, this lead may be positioned in and/or near a patient's heart or near an autonomic nerve within a patient's body and remote from the heart. In another example, the fourth lead can be configured to sense the phrenic nerve and/or activation of the diaphragm.

The right atrial lead 1004, as the name implies, is positioned in and/or passes through a patient's right atrium. The right atrial lead 1004 optionally senses atrial cardiac signals and/or provides right atrial chamber stimulation therapy. As shown in FIG. 10, the IMD 904 is coupled to implantable right atrial lead 1004 having, for example, an atrial tip electrode 1020, which typically is implanted in the patient's right atrial appendage. The lead 1004, as shown in FIG. 10, also includes an atrial ring electrode 1021. Of course, lead 1004 may have other electrodes as well. For example, the right atrial lead optionally includes a distal bifurcation having electrodes suitable for stimulation of autonomic nerves, non-myocardial tissue, other nerves, etc. In an alternative configuration, lead 1010 can be replaced with a mechanism for connecting the IMD to various other devices. For example, the mechanism can facilitate connecting IMD 904 to a drug pump for dispensing drugs into the patient in accordance with instructions received from the IMD. The skilled artisan should recognize various other configurations that may be employed which are consistent with the principles described above and below.

To sense atrial cardiac signals, ventricular cardiac signals and/or to provide multi-site pacing therapy, particularly on the left side of a patient's heart, the IMD 904 is coupled to a coronary sinus lead 1006 designed for placement in the coronary sinus and/or tributary veins of the coronary sinus. Thus, the coronary sinus lead 1006 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 1006 is optionally designed to receive atrial and ventricular cardiac signals and to deliver left ventricular pacing therapy using, for example, at least a left ventricular tip electrode 1022, left atrial pacing therapy using at least a left atrial ring electrode 1024, and shocking therapy using at least a left atrial coil electrode 1026. The coronary sinus lead 1006 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

IMD 904 is also shown in electrical communication with the patient's heart 1002 by way of an implantable right ventricular lead 1008 having, in this exemplary implementation, a right ventricular tip electrode 1028, a right ventricular ring electrode 1030, a right ventricular (RV) coil electrode 1032, and an SVC coil electrode 1034. Typically, the right ventricular lead 1008 is transvenously inserted into the heart 1002 to place the right ventricular tip electrode 1028 in the right ventricular apex so that the RV coil electrode 1032 will be positioned in the right ventricle and the SVC coil electrode 1034 will be positioned in the superior vena cava. Accordingly, the right ventricular lead 1008 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

FIG. 11 shows an exemplary, simplified block diagram depicting various components of IMD 904. The IMD 904 can be capable of treating both fast and slow arrhythmias with stimulation therapy, including cardioversion, defibrillation, and pacing stimulation. The IMD can be solely or further capable of sensing and/or delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable IMD. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 1100 for IMD 904 is often referred to as the "can", "case" or "case electrode", and may be programmably selected to act as the return electrode for all "unipolar"

modes. Housing 1100 may further be used as a return electrode alone or in combination with one or more of the coil electrodes 1026, 1032 and 1034 for shocking purposes. Housing 1100 further includes a connector (not shown) having a plurality of terminals 1101, 1102, 1104, 1106, 1108, 1112, 1114, 1116, 1118, 1121 (shown schematically and, for convenience, the names of the electrodes to which they are connected are shown next to the terminals).

To achieve right atrial sensing and/or pacing, the connector includes at least a right atrial tip terminal ($A_R$ TIP) 1101 adapted for connection to the atrial tip electrode 1020. A right atrial ring terminal ($A_R$ RING) 1102 is also shown, which is adapted for connection to the atrial ring electrode 1021. To achieve left chamber sensing, pacing and/or shocking, the connector includes at least a left ventricular tip terminal ($V_L$ TIP) 1104, a left atrial ring terminal ($A_L$ RING) 1106, and a left atrial shocking terminal ($A_L$ COIL) 1108, which are adapted for connection to the left ventricular tip electrode 1022, the left atrial ring electrode 1024, and the left atrial coil electrode 1026, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 1121).

To support right chamber sensing, pacing, and/or shocking, the connector further includes a right ventricular tip terminal ($V_R$ TIP) 1112, a right ventricular ring terminal ($V_R$ RING) 1114, a right ventricular shocking terminal (RV COIL) 1116, and a superior vena cava shocking terminal (SVC COIL) 1118, which are adapted for connection to the right ventricular tip electrode 1028, right ventricular ring electrode 1030, the RV coil electrode 1032, and the SVC coil electrode 1034, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 1121).

At the core of the IMD 904 is a programmable microcontroller 1120 that controls the various modes of stimulation therapy. As is well known in the art, microcontroller 1120 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 1120 includes the ability to process or monitor input signals (data or information) as controlled by a program code stored in a designated block of memory. The type of microcontroller is not critical to the described implementations. Rather, any suitable microcontroller(s) 1120 may be used that carries out the functions described herein. The use of microprocessor-based control circuits for performing timing and data analysis functions are well known in the art.

FIG. 11 also shows an atrial pulse generator 1122 and a ventricular pulse generator 1124 that generate pacing stimulation pulses for delivery by the right atrial lead 1004, the coronary sinus lead 1006, and/or the right ventricular lead 1008 via an electrode configuration switch 1126. It is understood that in order to provide stimulation therapy in each of the four chambers of the heart the atrial and ventricular pulse generators, 1122 and 1124, may include dedicated, independent pulse generators, multiplexed pulse generators, or shared pulse generators. The pulse generators 1122 and 1124 are controlled by the microcontroller 1120 via appropriate control signals 1128 and 1130, respectively, to trigger or inhibit the stimulation pulses.

Microcontroller 1120 further includes a plurality of modules 1132 that, when executed, perform various functions of the IMD. For instance, the modules can perform arrhythmia detection, timing control, capture detection, and/or morphology detection, among other functionalities.

The illustrated example specifically designates a timing control module 1134, an arrhythmia detection module 1136, a capture detection module 1138, an alert generation module 1140, and an alert management module 1141.

Timing control module 1134 controls the timing of the stimulation pulses (e.g., pacing rate, atrio-ventricular (AV) delay, atrial interconduction (A-A) delay, or ventricular interconduction (VV) delay, etc.) as well as to keep track of the timing of refractory periods, blanking intervals, noise detection windows, evoked response windows, alert intervals, marker channel timing, etc., which is well known in the art.

The arrhythmia detection module 1136 and the capture detection module 1138 can be utilized by the IMD 904 for detecting patient conditions and determining desirable times to administer various therapies such as pacing, defibrillation and/or in vivo dispensing of pharmaceuticals.

The alert generation module 1140 can be configured to compare parameter values relating to the patient to pre-established thresholds for the parameter values. In some instances the parameter values relating to the patient are derived from data sensed from the patient, such as IEGM data or blood pressure data. In other cases the parameters can relate to the patient in other ways. For example, the parameters can relate to a remaining functional life of the IMD's battery. In an instance where the patient's parameter values are less than or greater than a corresponding pre-established threshold then the alert generation module generates an alert. The alert can be communicated to the alert management module 1141 and/or communicated to an external device. Detailed examples of generating IMD-related alerts can be seen at U.S. Pat. No. 6,561,984 and U.S. Patent Publication No. 20070066913, among others.

The alert management module 1141 can be configured to perform some or all of the alert management functionality described above and below. For instance, the alert management module can utilize predefined parameters that specify how IMD-related alerts should be handled. Examples of such predefined parameters are described in relation to FIGS. 2-8. In some cases the predefined parameters define whether the IMD should immediately attempt to communicate the alert to an external device or whether the alert should be communicated to an external device at a next regularly scheduled time.

Electronic configuration switch 1126 includes a plurality of switches for connecting the desired electrodes to the appropriate I/O circuits, thereby providing complete electrode programmability. Accordingly, switch 1126, in response to a control signal 1142 from the microcontroller 1120, determines the polarity of the stimulation pulses (e.g., unipolar, bipolar, combipolar, etc.) by selectively closing the appropriate combination of switches (not shown) as is known in the art.

Atrial sensing circuits 1144 and ventricular sensing circuits 1146 may also be selectively coupled to the right atrial lead 1004, coronary sinus lead 1006, and the right ventricular lead 1008, through the switch 1126 for detecting the presence of cardiac activity (i.e., sensed biological data) in each of the four chambers of the heart. Accordingly, the atrial (ATR. SENSE) and ventricular (VTR. SENSE) sensing circuits, 1144 and 1146, may include dedicated sense amplifiers, multiplexed amplifiers, or shared amplifiers. Switch 1126 determines the "sensing polarity" of the cardiac signal by selectively closing the appropriate switches, as is also known in the art. In this way, the clinician may program the sensing polarity independent of the stimulation polarity. The sensing circuits (e.g., 1144 and 1146) are optionally capable of obtaining information (i.e., sensed biological data) indicative of tissue capture.

Each sensing circuit 1144 and 1146 preferably employs one or more low power, precision amplifiers with programmable gain and/or automatic gain control, bandpass filtering, and a threshold detection circuit, as known in the art, to selectively sense the cardiac signal of interest. The automatic gain control enables the IMD 904 to deal effectively with the problem of sensing the low amplitude signal characteristics of atrial or ventricular fibrillation. In such an instance, sensing the cardiac signal of interest generates sensed biological data.

The outputs of the atrial and ventricular sensing circuits 1144 and 1146 are connected to the microcontroller 1120, which, in turn, is able to trigger or inhibit the atrial and ventricular pulse generators 1122 and 1124, respectively, in a demand fashion in response to the absence or presence of cardiac activity in the appropriate chambers of the heart. Furthermore, as described herein, the microcontroller 1120 is also capable of analyzing information output from the sensing circuits 1144 and 1146 and/or a data acquisition system (introduced below) to determine or detect whether capture has occurred and to program a pulse, or pulses, in response to such determinations. The sensing circuits 1144 and 1146, in turn, receive control signals over signal lines 1148 and 1150 from the microcontroller 1120 for purposes of controlling the gain, threshold, polarization charge removal circuitry (not shown), and the timing of any blocking circuitry (not shown) coupled to the inputs of the sensing circuits, 1144 and 1146, as is known in the art.

For arrhythmia detection, IMD 904 utilizes the atrial and ventricular sensing circuits, 1144 and 1146, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals (i.e., sensed biological data) and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 1136 of the microcontroller 1120 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 1152. The data acquisition system 1152 is configured to acquire intracardiac electrogram (IEGM) signals, convert the raw analog data into a digital signal, and store the digital signals for later processing. The sensed cardiac signals can be thought of as sensed biological data whether the sensed cardiac signals are in analog or digital form. The data acquisition system 1152 is coupled to the right atrial lead 1004, the coronary sinus lead 1006, the right ventricular lead 1008 and/or the nerve or other tissue stimulation lead 1010 through the switch 1126 to sample cardiac signals across any pair of desired electrodes.

The microcontroller 1120 is further coupled to a memory 1160 by a suitable data/address bus(s) 1162, wherein the programmable operating parameters (i.e., supporting data) used by the microcontroller 1120 are stored and modified, as required, in order to customize the operation of the IMD 904 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 1002 within each respective tier of therapy.

Advantageously, operating parameters of the IMD 904 may be non-invasively programmed into the memory 1160 through a telemetry circuit 1164 in telemetric communication via communication link 1166 with an external device 202, such as a programmer, transtelephonic transceiver, or a diagnostic system analyzer. The microcontroller 1120 activates the telemetry circuit 1164 with a control signal 1168. The telemetry circuit 1164 advantageously allows a signal or data, such as alert from alert generation module 1140 to be sent to the external device 202 through an established communication link 1166. In such an instance, the alert management module 1141 can control functioning of the telemetry circuit based upon the predefined alert management parameters.

The IMD 904 can further include a physiologic sensor(s) 1170 to sense biological data including one or more of patient activity, patient posture, and respirations, among others. Microcontroller 1120 can utilize data received from the physiologic sensor(s) 1170 to adjust the various pacing parameters (such as rate, AV Delay, VV Delay, etc.) at which the atrial and ventricular pulse generators, 1122 and 1124, generate stimulation pulses.

While shown as being included within the IMD 904, it is to be understood that the physiologic sensor 1170 may also be external to the IMD 904, yet still be implanted within or carried by the patient. Examples of physiologic sensors that may be implemented in IMD 904 include known sensors that, for example, sense pressure, respiration rate, pH of blood, cardiac output, preload, afterload, contractility, oxygen levels, and so forth. Another sensor that may be used is one that detects activity variance, where an activity sensor is monitored to detect the low variance in the measurement corresponding to the sleep state and/or maintenance of a specific posture.

The physiological sensors 1170 optionally include biological data sensors for detecting movement and minute ventilation in the patient. The physiological sensors 1170 may include a position sensor and/or a minute ventilation (MV) sensor to sense minute ventilation, which is defined as the total volume of air that moves in and out of a patient's lungs in a minute. Sensed biological data generated by the position sensor and MV sensor are passed to the microcontroller 1120 for analysis in determining whether to adjust the pacing rate, etc and/or for processing by alert generation module 1140.

The IMD 904 optionally includes circuitry capable of sensing biological data in the form of heart sounds and/or vibration associated with events that produce heart sounds. Such circuitry may include an accelerometer as conventionally used for patient position and/or activity determinations.

While an accelerometer may be included in the case of an IMD in the form of an implantable pulse generator device, alternatively, an accelerometer communicates with such a device via a lead or through electrical signals conducted by body tissue and/or fluid. In the latter instance, the accelerometer may be positioned to advantageously sense vibrations associated with cardiac events. For example, an epicardial accelerometer may have improved signal to noise for cardiac events compared to an accelerometer housed in a case of an implanted pulse generator device. Information acquired through use of an accelerometer(s) may be stored by an implantable device and utilized for selecting or adjusting therapy and/or communicated to a device manager (e.g., device programmer, etc.).

IMD 904 may also include, or be in communication with, an implanted drug pump 1174 or other drug delivery mechanism to effect patient therapy. The drug pump can be activated in various scenarios, such as when a heart failure condition is detected. Further, IMD-related alerts can be generated pertaining to the functionality of the drug pump. For instance, an IMD-related alert can be generated indicating that a remaining volume of drug in the drug pump is below a pre-established threshold.

The IMD 904 additionally includes a battery 1176 that provides operating power to all of the circuits shown in FIG. 11. For the IMD 904, which employs shocking therapy, the battery 1176 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 1176 also desirably has a predictable discharge characteristic so that elective replacement time can be detected.

The IMD 904 can further include magnet detection circuitry (not shown), coupled to the microcontroller 1120, to detect when a magnet is placed over the IMD 904. A magnet may be used by a clinician to perform various test functions of the IMD 904 and/or to signal the microcontroller 1120 that the external device 202 is in place to receive or transmit data to the microcontroller 1120 through the telemetry circuits 1164.

The IMD 904 further includes an impedance measuring circuit 1178 that is enabled by the microcontroller 1120 via a control signal 1180. The known uses for an impedance measuring circuit 1178 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance, such as for determining shock thresholds, (HF indications—pulmonary edema and other factors); detecting when the device has been implanted; measuring stroke volume; and detecting the opening of heart valves, etc. The impedance measuring circuit 1178 is advantageously coupled to the switch 1126 so that any desired electrode may be used.

In the case where the IMD 904 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 1120 further controls a shocking circuit 1182 by way of a control signal 1184. The shocking circuit 1182 generates shocking pulses in a range of joules, for example, conventionally up to about 40 J, as controlled by the microcontroller 1120. Such shocking pulses are applied to the patient's heart 1002 through at least two shocking electrodes, and as shown in this embodiment, selected from the left atrial coil electrode 1026, the RV coil electrode 1032, and/or the SVC coil electrode 1034. As noted above, the housing 1100 may act as an active electrode in combination with the RV electrode 1032, or as part of a split electrical vector using the SVC coil electrode 1034 or the left atrial coil electrode 1026 (i.e., using the RV electrode as a common electrode).

Cardioversion level shocks are generally considered to be of low to moderate energy level (so as to minimize battery drain and the more rapid delivery of the shock if the lower energy levels are effective in restoring a normal rhythm), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 1120 is capable of controlling the synchronous or asynchronous delivery of the shocking pulses.

In low-energy cardioversion, an IMD typically delivers a cardioversion stimulus (e.g., 0.1 to 5 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the IMD initiates defibrillation therapy.

While an IMD may reserve defibrillation as a latter tier therapy, it may use defibrillation as a first-tier therapy for VF. In general, an IMD does not synchronize defibrillation therapy with any given portion of an ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Exemplary External Medical Device

Figure 12:
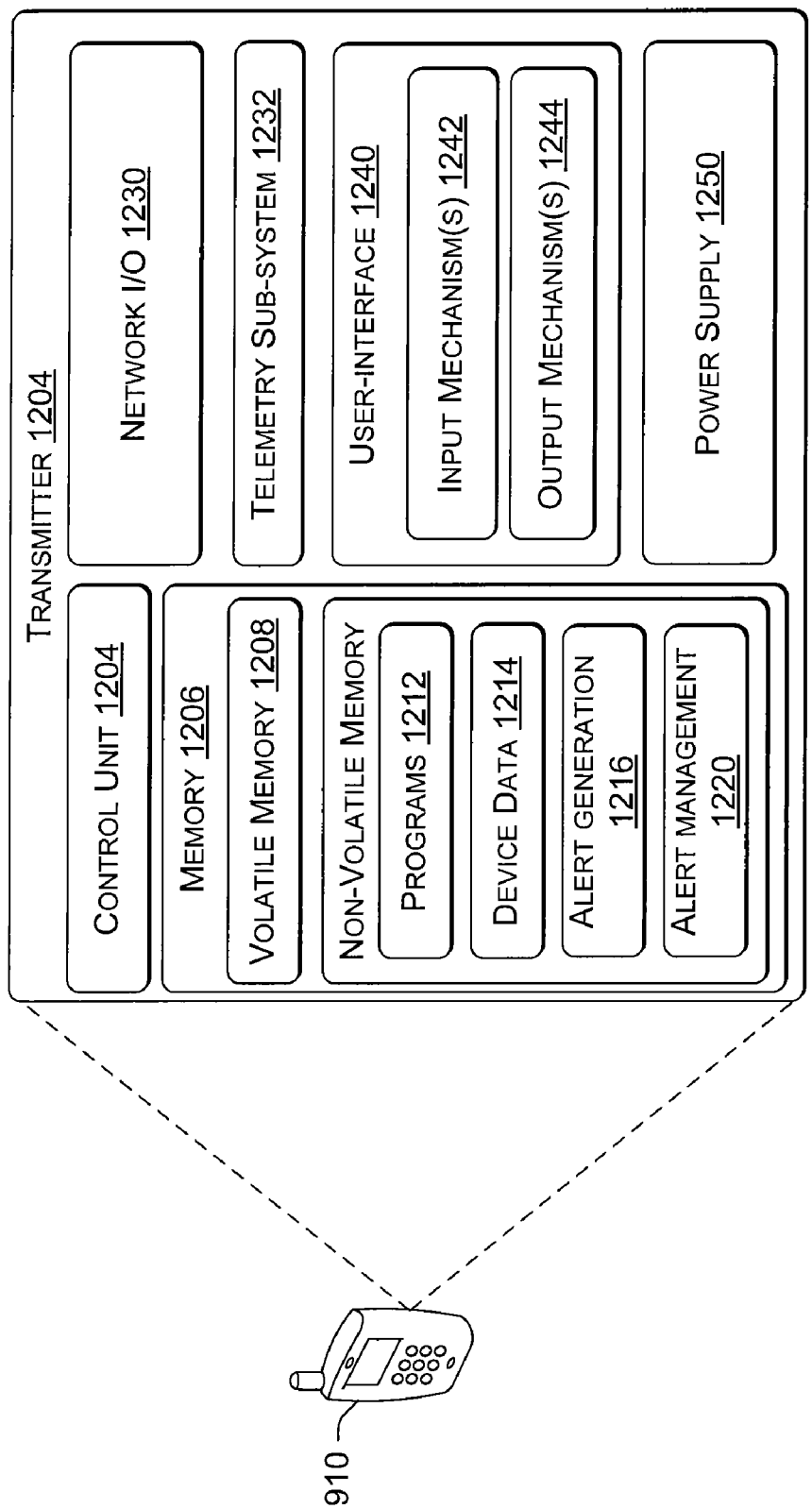
FIG. 12 shows an exemplary external medical device configured to manage IMD related alerts in accordance with some implementations.

FIG. 12 describes functional components of an exemplary external medical device in the form of transmitter 910 in more detail. The described components can also be implemented in other external medical device configurations, such as programmer 106 and device manager 108 introduced in relation to FIG. 1. Similarly, some or all of the functionality of transmitter 910 can be manifested in the servers and personal computers of FIGS. 1 and 9. The skilled artisan should recognize still other medical devices that are compatible with the concepts described above and below. In this instance, transmitter 910 includes a processing or control unit 1204 and memory 1206. The control unit 1204 controls operations carried out by the transmitter 910, such as programming an IMD, gathering data from the IMD, and/or carrying out various testing or diagnostic functions. Memory 1206 includes both volatile memory 1208 (e.g., RAM) and non-volatile memory 1210 (e.g., ROM, EEPROM, Flash, disk, optical discs, persistent storage, etc.).

Programs, operating parameters, and algorithms 1212, which are used in controlling the programming and testing functions, may be stored in memory 1206. When a program is running, various instructions are loaded into volatile memory 1208 and executed by control unit 1204. IMD-related data or device data 1214 collected from the IMD may be stored in memory 1206 for subsequent analysis and/or transfer to other computing systems.

In this particular configuration, an alert generation module 1216 and an alert management module 1220 are also stored in memory 1206. The alert generation module 1216 can be configured to compare parameter values relating to the patient to pre-established thresholds for the parameter values. In an instance where the patient's parameter values are less than or greater than a corresponding pre-established threshold then the alert generation module generates an alert. In one case the parameter can relate to a length of elapsed time since the transmitter last received a communication from the IMD. If the elapsed time is greater than the pre-established parameter then an alert can be generated. The alert can be communicated to the alert management module 1141 of the IMD (e.g., the IMD 904 of FIG. 9) and/or communicated to an external device (e.g., the transmitter 910 of FIG. 9).

The alert management module 1220 can be configured to perform some or all of the alert management functionality described above and below. For instance, the alert management module can utilize predefined parameters that specify how IMD-related alerts should be handled. Examples of such predefined parameters are described in relation to FIGS. 2-8.

The transmitter 910 may further be equipped with a network I/O connection 1230 to facilitate communication with a network and/or other computing devices such as a server(s). The network I/O 1222 may be a wire-based connection (e.g., network card, modem, etc.) or a wireless connection, such as a Bluetooth device.

The transmitter 910 can be equipped with a telemetry sub-system 1232 that manages communications between transmitter 910 and an IMD. The telemetry sub-system 1232 can include telemetry hardware such as telemetry wands and/or other telemetry mechanisms for communicating with the IMD.

The transmitter 910 may also include a user interface 1240 which includes one or more user input mechanism(s) 1242 and one or more output mechanisms 1244. Input mechanisms allow user input to be received by the transmitter. Examples of mechanisms for user input include, but are not limited to keypads, buttons, selection wheels, touch pads, touch screens or touch-sensitive screens, and voice recognition systems, among others. Output mechanisms 1244 allow information to be provided from the transmitter for user observation. The output mechanisms generate signals such as audio and/or visual signals for the user which, for example, can relate to a patient condition associated with the IMD or to transmitter operations performed by users. The output mechanisms can also generate signals for conveying various parameter value changes to the user and/or various resulting longevity estimation information. Various examples are described above and below. Examples of output mechanisms include, but are not limited to, monitors, LEDs, speakers, and/or printing mechanisms, among others. For purposes of characterization, distinct input and output mechanisms are described, but in some instances, a single mechanism performs both functions. For instance, the user interface can be manifested as a touch-sensitive screen which performs both input and output functions.

The components illustrated in FIG. 12 are interconnected via one or more buses (not shown) and are powered by a power supply 1250. Further, while aspects of transmitter 910 are described in relation to modules implemented by transmitter 910, various modules could alternatively or additionally be implemented as freestanding components such as application specific integrated circuits (ASIC). Additionally, various aspects of the methods and systems described throughout this disclosure may be implemented in computer software or firmware as computer-executable instructions. The instructions can be stored on any computer-readable storage media. When executed, these instructions direct the transmitter to perform various functions and tasks described above and below.

Operation

Figure 13:
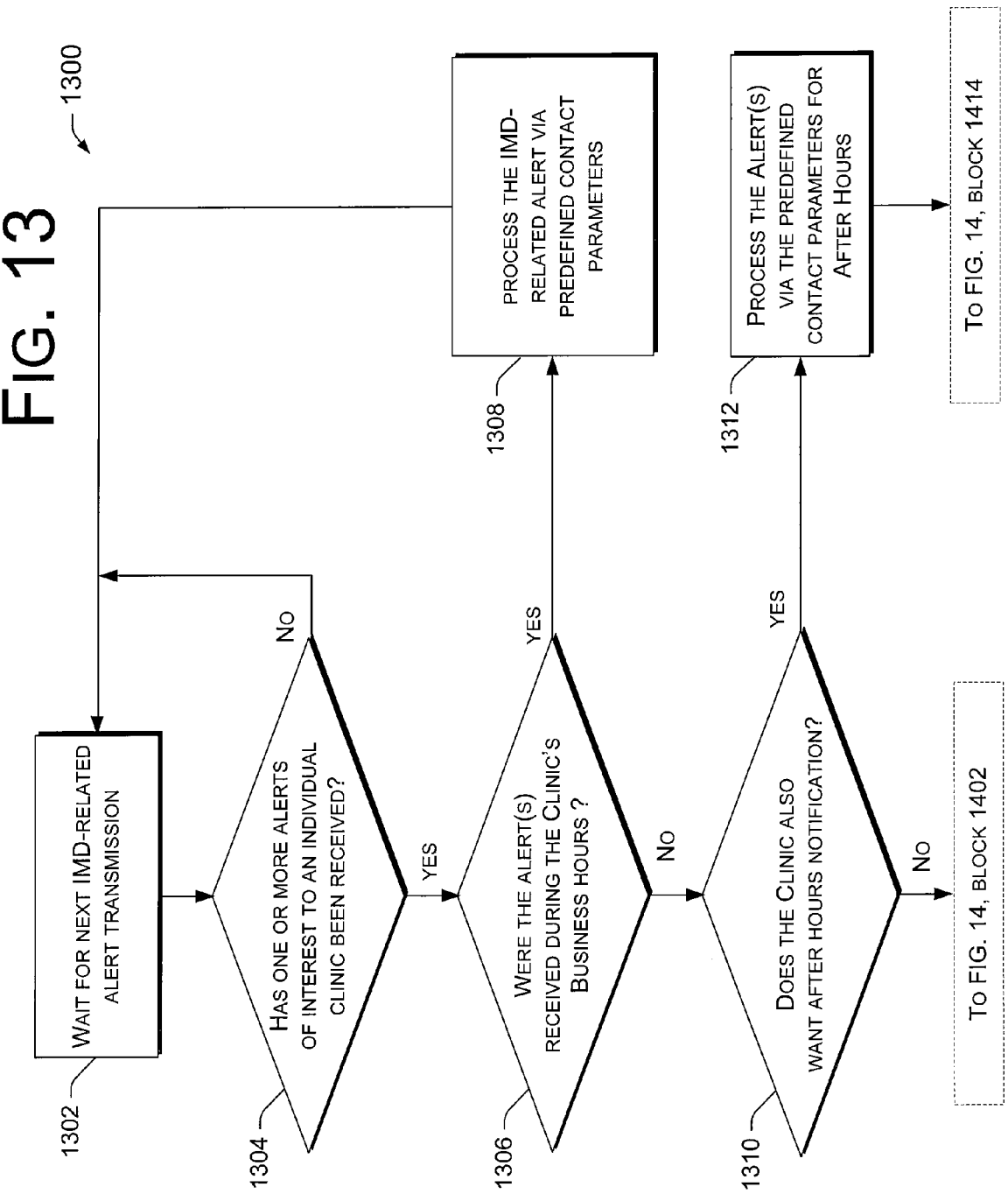
Figure 14:
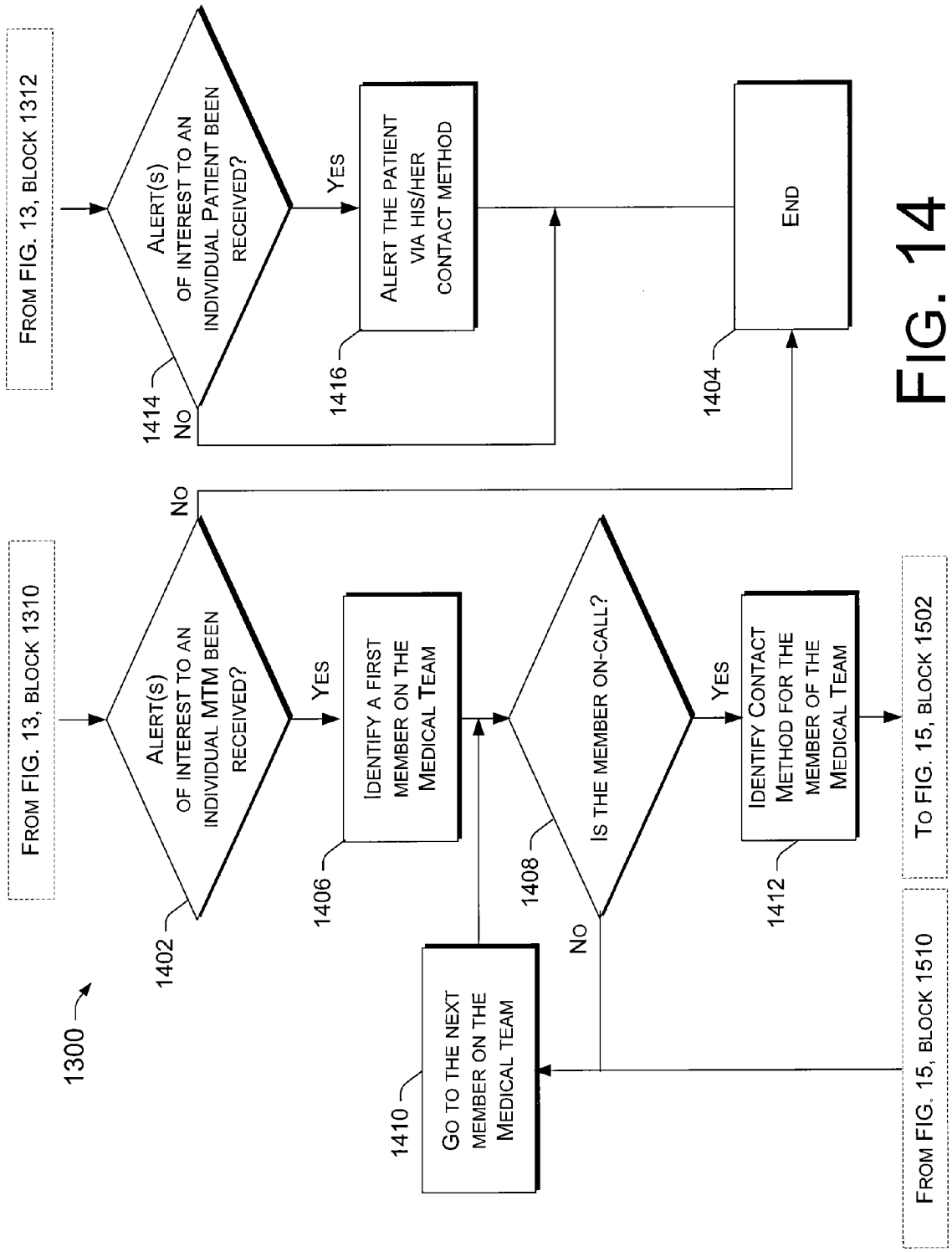

FIGS. 13-15 show an exemplary method or technique 1300 for implementing automated management of IMD-related alerts. The following description explains how individual IMD-related alerts are automatically managed in accordance with predefined parameters. Method 1300 is described from a clinical perspective that is customized for individual clinicians and/or patients. Assume for purposes of explanation that the clinic in this example is a cardiac clinic that includes multiple electrophysiologists (EPs). This is but one organizational configuration and other methods that are consistent with the inventive concepts should become apparent to the skilled artisan in light of the description above and below.

This method 1300 may be implemented in connection with any suitably configured external medical devices and/or systems of external medical devices and/or IMDs. Non-limiting examples of IMDs, external medical devices, and/or systems upon which the method can be implemented are described above in relation to FIGS. 1 and 9. Further, the method is implemented utilizing predefined parameters. Examples of techniques for predefining the parameter values via a graphical user interface are described above in relation to FIGS. 3-8. A set of predefined parameters can be utilized for automatically managing many different alerts. The set of predefined parameters can be thought of as generic since they can be utilized in managing many different IMD-related alerts. Parsing individual IMD-related alerts through the predefined parameters in a cascading fashion can allow the individual alerts to be managed in a customized fashion utilizing the generic predefined parameters.

The order in which the method 1300 is described is not intended to be construed as a limitation, and any number of the described blocks can be combined in any order to implement the method, or an alternate method. Furthermore, the methods can be implemented in any suitable hardware, software, firmware, or combination thereof such that a computing device can implement the method. In one case, the method is stored on a computer-readable storage media as a set of instructions such that execution by a computing device, such as an external medical device, causes the computing device to perform the method. In some cases, the method is performed via a web-based solution, while in other cases the method is performed via instructions stored upon various devices involved in performing the method.

At block 1302, the method waits for an IMD-related alert to be transmitted. IMD-related alerts can be generated by different devices. For example, the IMD can generate alerts and a transmitter, programmer or other device can also generate alerts. Transmission of an IMD-related alert can occur between the IMD and an external device and/or between two external devices.

Block 1304 queries whether one or more IMD-related alerts of interest to an individual clinic has been received. Various techniques can be utilized to determine whether an IMD-related alert relates to an individual clinic. For instance, the IMD-related alert can be associated with a unique identifier to indicate the IMD and/or the patient to which the alert relates. The unique identifier can be utilized with a data table or other referencing mechanism to determine the patient to which the alert relates. The data table can further convey which clinic the patient is associated with. An example of a screenshot that allows various parameters to be established at various organizational levels, such as the clinic level is described above in relation to FIG. 4. In this case, if no IMD-related alerts have been received relating to the clinic then the method returns to block 1302. In an instance where an IMD-related alert is received then the method proceeds to block 1306.

At block 1306 the method queries whether the alert(s) was received during the clinic's business hours. An example of a screenshot that allows a time parameter to be pre-defined, such as in relation to business and non-business hours is described above in relation to FIG. 7. If the IMD-related alert was received during the clinic's business hours (i.e., yes at 1306) then the method proceeds to block 1308, otherwise (i.e., a "no" condition at 1306) the method proceeds to block 1310.

In a case where the IMD-related alert was received during business hours then the method proceeds to block 1308. At block 1308 the method processes the IMD-related alert via predefined contact parameters for the clinic relating to business hours notification. The predefined contact parameters relate to what contact mechanisms to use to contact the clinic during business hours. Contact can be made via any combination of contact mechanisms. For example, the contact for the IMD-related alert can be achieved via updating a webpage, telephoning, faxing, paging, and text messaging among others. An example of predefining contact mechanisms is described above in relation to FIG. 8.

In an alternative case where the IMD-related alert was not received during business hours then the method proceeds to block 1310. At block 1310 the method queries whether the clinic also wants after hours (i.e., non-business hours) notification. If the clinic wants after hours notification (i.e., has predefined to receive after hours notification) then the method proceeds to block 1312. If the clinic does not want after hours notification (i.e., "no" at 1310), then the method proceeds to block 1402 of FIG. 14.

In an instance where the clinic does want after hours notification, then block 1312 processes the alert via the contact parameters predefined for after hours. The after hours contacts can be predefined via various delivery mechanisms examples of which are described above in relation to FIG. 8. After processing the IMD-related alert at block 1312 the method proceeds to block 1414 of FIG. 14.

Turning now to block 1402 of FIG. 14 the method queries whether one or more alerts of interest to a medical team member have been received. The medical team can be thought of as a sub-set of the clinic's overall staff that is in charge of particular patients. This block allows groups of EP's to customize their alert management if desired. Examples of predefinable parameters for customizing automated alert management are described above in relation to FIGS. 2-8. In an instance where the IMD-related alert does not correspond to a medical team that customized their alert management (i.e., "no" at block 1402) then the method ends at 1404. In an instance where the IMD-related alert corresponds to a medical team that has customized their alert management (i.e., "yes" at block 1402) then the method proceeds to block 1406.

At block 1406, the method identifies a first member on the medical team. Various data tables or equivalents can be utilized to identify the first member of the medical team.

At block 1408 the method queries whether the member (in this case the first member) is on call. In an instance where the first member is not on call (i.e., "no" at block 1408) then the method proceeds to block 1410, otherwise the method proceeds to block 1412. In the case where the first team member is not on call the method goes to the next member on the medical team at 1410. The method then wraps back into block 1408 and queries whether the member (in this case the next member) is on call.

In an instance where the team member (such as the first team member) is on call then the method identifies the contact method for the member at block 1412. Various examples of contact methods are described in relation to contact mechanisms in the above description of FIG. 8.

Turning now to block 1414 (which flows from block 1312 of FIG. 13) the method queries whether one or more IMD-related alerts of interest to an individual patient has been received. This block allows individual patients that have predefined parameters to be handled in accordance with those parameters. In an instance where an alert of interest has been received (i.e., "yes" at 1414) then the method proceeds to block 1416 otherwise the method ends at 1404.

At block 1416 the method alerts the patient via their contact method. The contact method can be predefined such as via the contact mechanisms window described above in relation to FIG. 8. Upon contacting the patient according to block 1416, this portion of the method ends at 1404.

Turning now to block 1502 of FIG. 15 where the method, continuing from block 1412, attempts to send alert(s) to the team member via the identified contact method. In some cases the contact method can further include retry parameters for the selected method. These retry parameters define further action in cases where the contact is unsuccessful. For instance, in a fax related scenario, the retry parameters can specify a number of times that the fax should be resent if previous attempts are unsuccessful. Further, the retry parameter can specify that the method obtain related information, such as a fax offline message or a fax offline message. In an email scenario, the method can look for an email address invalid message or email down message.

At block 1504 the method queries whether the contact is successfully accomplished. For instance, if the specified contact method involves faxing, then the method can judge whether the fax was successful based upon whether a fax handshake occurred. In another case, where voice messaging is utilized as the contact method, the team member may be required to enter his/her physician ID to ensure that the intended recipient was the actual recipient. Various other techniques for establishing whether the contact was successfully accomplished should be recognized by the skilled artisan. In an instance where contact was successfully accomplished ("yes" at block 1504) then this portion of the method ends at 1506, otherwise the method proceeds to block 1508.

At block 1508 the method queries whether the maximum number of attempts (for contact) has been exceeded. The maximum number of attempts can be predefined in the retry parameters. In an instance where the maximum number of attempts has been exceeded ("yes" at 1508) then the method ends at 1506, otherwise the method proceeds to block 1510.

At block 1510 the method queries whether an intervening web acknowledgement has been received. In an instance where an intervening acknowledgment confirms that the contact has been received then the method ends at 1506, otherwise the method returns to block 1410 of FIG. 14. Block 1410 allows the process to go to the next medical team member and return into the method above block 1408 for the next team member.

In summary, exemplary methods allow a set of parameters to be defined for managing alerts. In one case, a user interface is generated that allows a user to define values for the multiple parameters. The defined parameters can be utilized to manage a wide range of IMD-related alerts and hence can be thought of as generic to the alerts. However, the method can achieve customized management of an individual IMD-related alert by parsing the alert through the predefined parameters. The resulting management path can be thought of as customized to the individual alert even though it is derived from a generic set of parameters.

CONCLUSION

Exemplary techniques, methods, devices, systems, etc., pertaining to automatically managing IMD-related alerts are described above. Although techniques, methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A system comprising:
   a mechanism for receiving an alert relating to a patient's implantable medical device (IMD);
   a mechanism for determining at least one recipient from a plurality of recipients for the alert based upon a first predefined parameter, wherein the first predefined parameter comprises a temporal parameter; and,
   a mechanism for selecting a contact mechanism for communicating the alert to the recipient based upon a second predefined parameter.

2. The system of claim 1, wherein the mechanism for receiving is configured to receive the alert directly from the IMD or from a device that interrogated the IMD.

3. The system of claim 1, wherein the first predefined parameter includes temporal parameters.

4. The system of claim 3, wherein the temporal parameters specify the recipients based upon one or more of business hours versus non-business hours and calendar days.

5. The system of claim 1, wherein the first and second predefined parameters are applicable to any type of alert relating to the patient's IMD.

6. The system of claim 1, wherein the first and second predefined parameters are established by a clinical group responsible for care of the patient associated with the IMD.

7. The system of claim 1, wherein the first and second predefined parameters are established by a clinical group responsible for care of the patient associated with the IMD and are customizable by an individual clinician of the clinical group that is responsible for the patient.

8. The system of claim 1, wherein the second predefined parameter specifies delivery mechanisms for sending the alert to the recipients.

9. The system of claim 8, wherein the delivery mechanisms comprise one or more of: faxing, emailing, telephoning, and, text messaging.

10. The system of claim 1, further comprising a mechanism for confirming whether the recipients received the alert.

11. A method comprising:
    receiving an implantable medical device related alert; and,
    cascading the implantable medical device alert through a set of management parameters that determine a recipient from a plurality of recipients and a contact mechanism for the recipient based upon the parameters, wherein at least one of the management parameters comprises a temporal parameter; and
    based on the cascading, communicating the alert.

12. The method of claim 11, wherein the receiving comprises receiving the implantable medical device related alert from an implantable medical device.

13. The method of claim 11, wherein the receiving and the cascading are accomplished by a single medical device.

14. A system comprising:
    means for receiving an alert from an implantable medical device;
    means for cascading the alert through a set of management parameters and for determining a recipient from a plurality of recipients and a contact mechanism for the recipient based upon the parameters, wherein at least one of the management parameters comprises a temporal parameter; and
    means for communicating the alert based on the means for determining.

* * * * *